(12) United States Patent
Babu et al.

(10) Patent No.: US 9,804,155 B2
(45) Date of Patent: Oct. 31, 2017

(54) METHODS AND DEVICES FOR USING MUCOLYTIC AGENTS INCLUDING N-ACETYL CYSTEINE (NAC)

(71) Applicant: Rapid Pathogen Screening, Inc., Sarasota, FL (US)

(72) Inventors: Uma Mahesh Babu, Bradenton, FL (US); Robert P. Sambursky, Bradenton, FL (US)

(73) Assignee: RAPID PATHOGEN SCREENING, INC., Sarasota, FL (US)

( * ) Notice: Subject to any disclaimer, the term of this patent is extended or adjusted under 35 U.S.C. 154(b) by 280 days.

(21) Appl. No.: 14/805,708

(22) Filed: Jul. 22, 2015

(65) Prior Publication Data

US 2015/0323527 A1 Nov. 12, 2015

Related U.S. Application Data

(60) Division of application No. 13/463,126, filed on May 3, 2012, which is a continuation-in-part of application No. 12/502,662, filed on Jul. 14, 2009, now Pat. No. 8,614,101, which is a continuation-in-part of application No. 12/469,207, filed on May 20, 2009, now abandoned, and a continuation-in-part of application No. 12/481,631, filed on Jun. 10, 2009,
(Continued)

(51) Int. Cl.
*G01N 33/558* (2006.01)
*G01N 33/569* (2006.01)
*B01L 3/00* (2006.01)

(52) U.S. Cl.
CPC ..... *G01N 33/558* (2013.01); *G01N 33/56911* (2013.01); *G01N 33/56983* (2013.01); *B01L 3/5023* (2013.01); *Y10T 436/25125* (2015.01)

(58) Field of Classification Search
None
See application file for complete search history.

(56) References Cited

U.S. PATENT DOCUMENTS

| 4,094,647 A | 6/1978 | Deutsch et al. |
| 4,861,711 A | 8/1989 | Friesen et al. |

(Continued)

FOREIGN PATENT DOCUMENTS

| DE | 19622503 C2 | 7/1998 |
| EP | 1489416 A1 | 12/2004 |

(Continued)

OTHER PUBLICATIONS

"FTA Nucleic Acid Collection, Storage and Purification," Whatman website, http://whatman.com/products.aspx?PID=108.
(Continued)

*Primary Examiner* — Chris L Chin
(74) *Attorney, Agent, or Firm* — Brown & Michaels, PC

(57) ABSTRACT

Devices and methods incorporate mucolytic agents into a point-of-care testing device. The sample is loaded, and then the sample travels until it encounters one or more lysis agents and/or mucolytic agents. The mucolytic agent is preferably pre-loaded onto the collection device. In a preferred embodiment, the mucolytic agent is localized between the sample application zone and the conjugate zone. In embodiments with a sample compressor, one or more mucolytic agents may be pre-loaded and dried on the sample compressor, the sample collector, in various locations on the test strip, or in the running buffer.

4 Claims, 22 Drawing Sheets

Related U.S. Application Data now Pat. No. 8,470,608, said application No. 13/463,126 is a continuation-in-part of application No. 12/958,454, filed on Dec. 2, 2010, now Pat. No. 8,609,433.

(60) Provisional application No. 61/481,907, filed on May 3, 2011, provisional application No. 61/080,879, filed on Jul. 15, 2008, provisional application No. 61/098,935, filed on Sep. 22, 2008, provisional application No. 61/179,059, filed on May 18, 2009, provisional application No. 61/071,833, filed on May 20, 2008, provisional application No. 61/060,258, filed on Jun. 10, 2008, provisional application No. 61/266,641, filed on Dec. 4, 2009, provisional application No. 61/331,966, filed on May 6, 2010, provisional application No. 61/352,093, filed on Jun. 7, 2010, provisional application No. 61/392,981, filed on Oct. 14, 2010.

(56) References Cited

U.S. PATENT DOCUMENTS

| | | |
|---|---|---|
| 4,960,691 A | 10/1990 | Gordon et al. |
| 5,120,643 A | 6/1992 | Ching et al. |
| 5,496,562 A | 3/1996 | Burgoyne |
| 5,559,041 A | 9/1996 | Kang |
| 5,607,863 A | 3/1997 | Chandler |
| 5,637,469 A | 6/1997 | Wilding et al. |
| 5,695,949 A | 12/1997 | Galen et al. |
| 5,698,537 A | 12/1997 | Pruss |
| 5,714,341 A | 2/1998 | Thieme et al. |
| 5,756,126 A | 5/1998 | Burgoyne |
| 5,807,527 A | 9/1998 | Burgoyne |
| 5,824,268 A | 10/1998 | Bernstein et al. |
| 5,869,345 A | 2/1999 | Chandler |
| 5,939,252 A | 8/1999 | Lennon et al. |
| 5,972,386 A | 10/1999 | Burgoyne |
| 5,985,327 A | 11/1999 | Burgoyne |
| 6,106,779 A | 8/2000 | Buechler et al. |
| 6,350,578 B1 | 2/2002 | Stark et al. |
| 6,358,752 B1 | 3/2002 | Durst et al. |
| 6,368,876 B1 | 4/2002 | Huang et al. |
| 6,514,773 B1 | 2/2003 | Klein et al. |
| 6,875,619 B2 | 4/2005 | Blackburn |
| 7,374,950 B2 | 5/2008 | Kang et al. |
| 7,379,167 B2 | 5/2008 | Mawhirt et al. |
| 7,393,697 B2 | 7/2008 | Charlton |
| 7,425,302 B2 | 9/2008 | Piasio et al. |
| 7,723,124 B2 | 5/2010 | Aberl et al. |
| 7,939,342 B2 | 5/2011 | Song et al. |
| 2003/0027866 A1 | 2/2003 | Johnson et al. |
| 2003/0104506 A1 | 6/2003 | Durst et al. |
| 2003/0186463 A1 | 10/2003 | Hudak et al. |
| 2004/0110167 A1 | 6/2004 | Gerdes et al. |
| 2004/0156037 A1 | 8/2004 | Mawhirt et al. |
| 2004/0241779 A1 | 12/2004 | Piasio et al. |
| 2005/0227223 A1 | 10/2005 | Miyawaki |
| 2005/0239056 A1 | 10/2005 | Piasio et al. |
| 2006/0160078 A1 | 7/2006 | Cardy et al. |
| 2006/0240569 A1 | 10/2006 | Goldenbaum et al. |
| 2007/0059682 A1 | 3/2007 | Aberl et al. |
| 2007/0141564 A1 | 6/2007 | Aberl et al. |
| 2007/0264629 A1 | 11/2007 | Holmes et al. |
| 2008/0085525 A1 | 4/2008 | Van Herwijnen |
| 2008/0199851 A1 | 8/2008 | Egan et al. |
| 2009/0011436 A1 | 1/2009 | Piasio et al. |
| 2009/0232702 A1 | 9/2009 | Wu et al. |
| 2010/0143891 A1 | 6/2010 | Aberl et al. |
| 2010/0279308 A1 | 11/2010 | Morrow et al. |
| 2010/0291536 A1 | 11/2010 | Viljoen et al. |

FOREIGN PATENT DOCUMENTS

| | | | |
|---|---|---|---|
| JP | 2000502452 | A | 2/2000 |
| JP | 2005017248 | A | 1/2005 |
| WO | 9723781 | A1 | 7/1997 |
| WO | 03073817 | A2 | 9/2003 |
| WO | 2004076054 | A2 | 9/2004 |
| WO | 2006115866 | A1 | 11/2006 |
| WO | 2007070117 | A1 | 6/2007 |
| WO | 2008014709 | A1 | 2/2008 |
| WO | 2009044167 | A1 | 4/2009 |

OTHER PUBLICATIONS

Barnard, et al., "Development of an Oligonucleotide-Based SNP Detection Method on Lateral Flow Strips Using Hexapet Tags," Point of Care, vol. 4, No. 3, pp. 108-118 (Sep. 2005).

Berezovski, et al., "Cell lysis inside the capillary facilitated by transverse diffusion of laminar flow profiles (TDLFP)," Anal Bioanal Chem (2007) 387:91-96.

Chieux V, Hober D, Harvey J, Lion G, Lucidarme D, Forzy G, Duhamel M, Cousin J, Ducoulombier H, Wattre P. The MxA protein levels in whole blood lysates of patients with various viral infections. J Virol Methods. 1998;70:183-191.

Extended European Search Report for application No. 09798691.3, European Patent Office, dated Feb. 10, 2012.

International Search Report and Written Opinion dated Mar. 12, 2010, International Application No. PCT/US2009/050653.

Karle, et al., "Application of FTA-based Technology for Sample Collection, Transport, Purification, and Storage of PCR-ready Plant DNA" (Nov. 2003).

O'Mahony, et al., "Integration of Bacteria Capture via Filtration and in Situ Lysis for Recovery of Plasmid DNA under Industry-Compatible Conditions," Biotechnol. Prog. 2007, 23, pp. 895-903.

Sambursky et al., "The RPS Adeno Detector for Diagnosing Adenoviral Conjunctivitis", Ophthalmology, vol. 113, No. 10, pp. 1758-1764 (Oct. 2006).

Sambursky, "510-K Summary of Safety and Effectiveness" (Sep. 14, 2005).

Uchio, et al., "Rapid Diagnosis of Adenoviral Conjunctivitis on Conjunctival Swabs by 10-Minute Immunochromatography," Opthalmology, vol. 104, No. 8, Aug. 1997, pp. 1294-1299.

Udeh et al., "Cost Effectiveness of a Point-of-Care Test for Adenoviral Conjunctivitis", The American Journal of the Medical ciences, vol. 336, No. 3, pp. 254-264 (Sep. 2008).

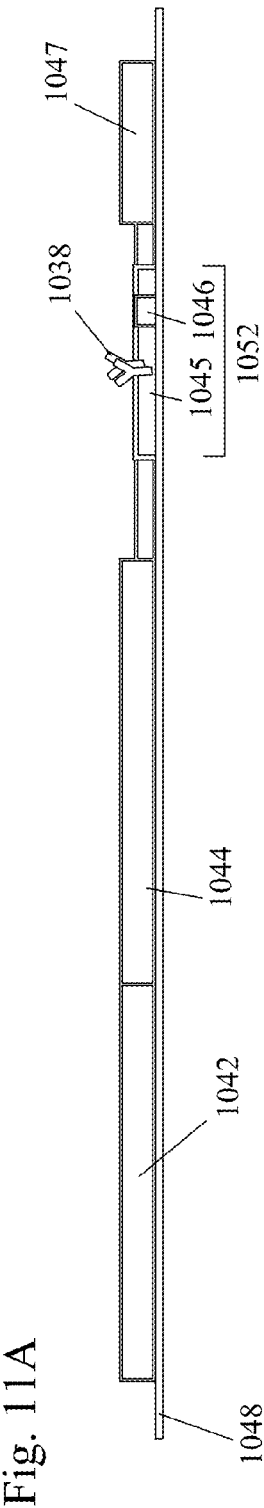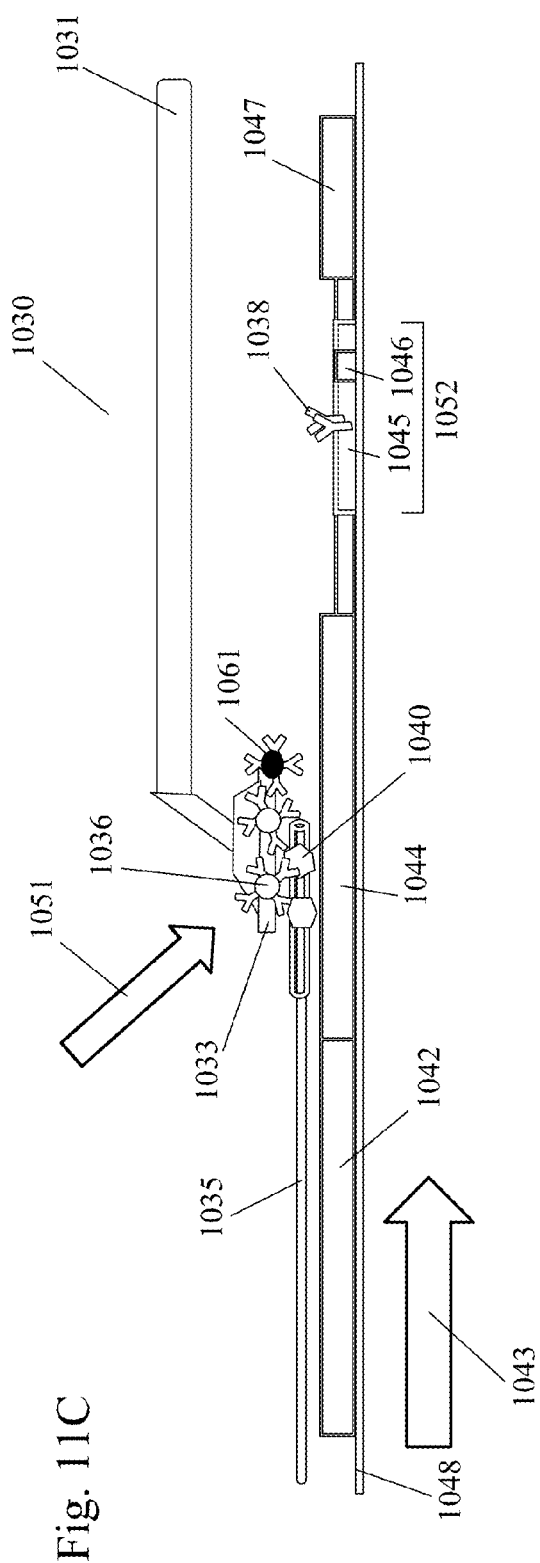

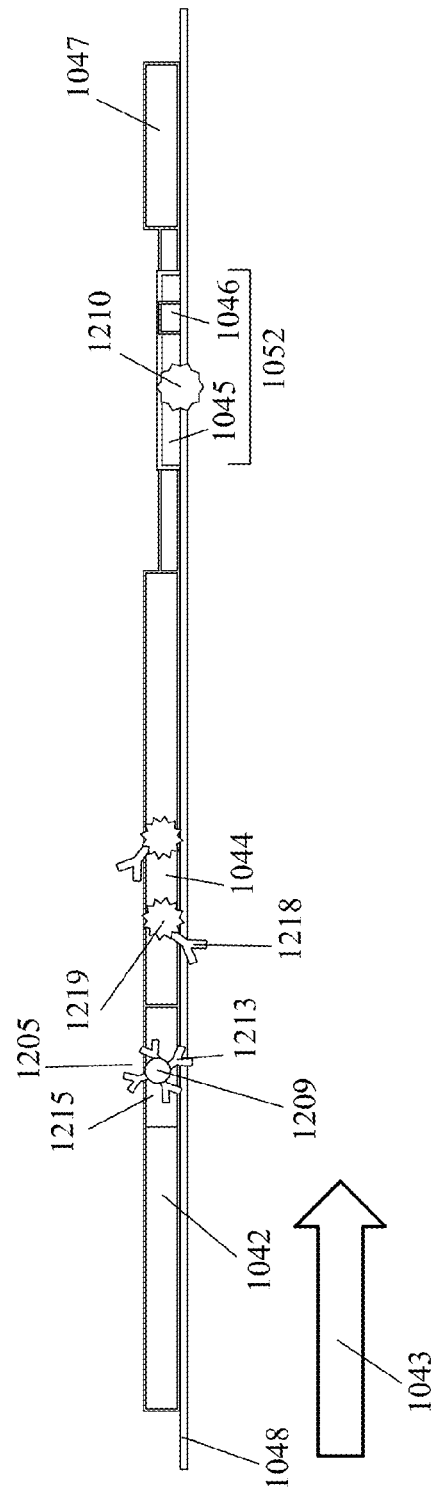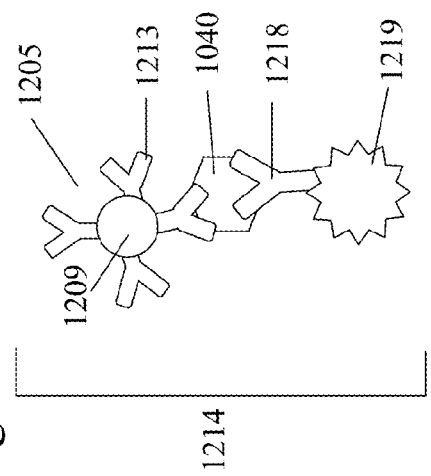
Fig. 12A
Fig. 12B

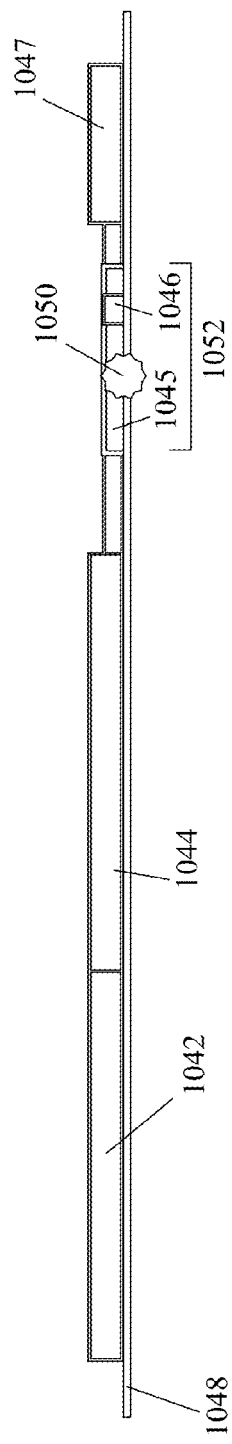
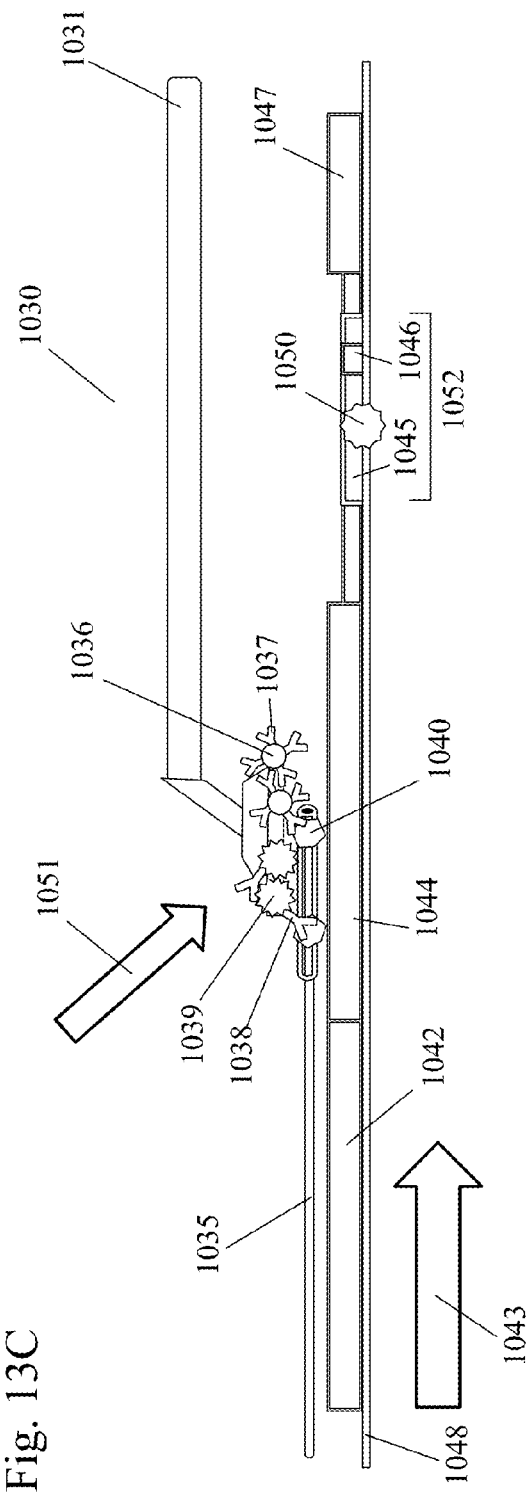

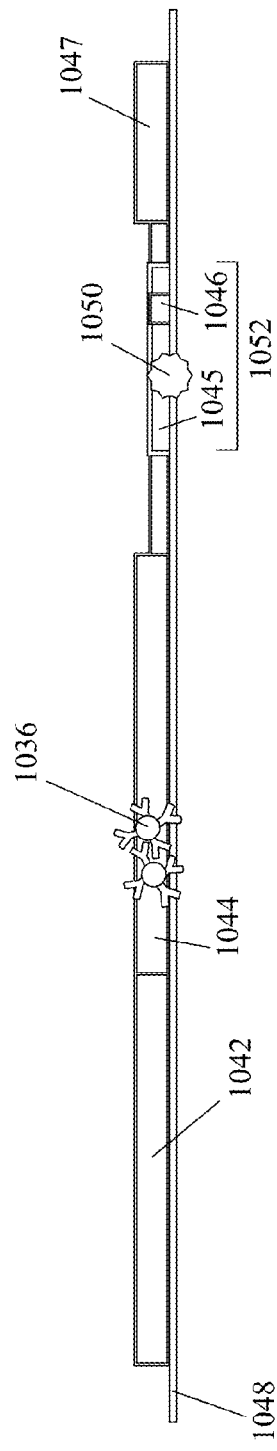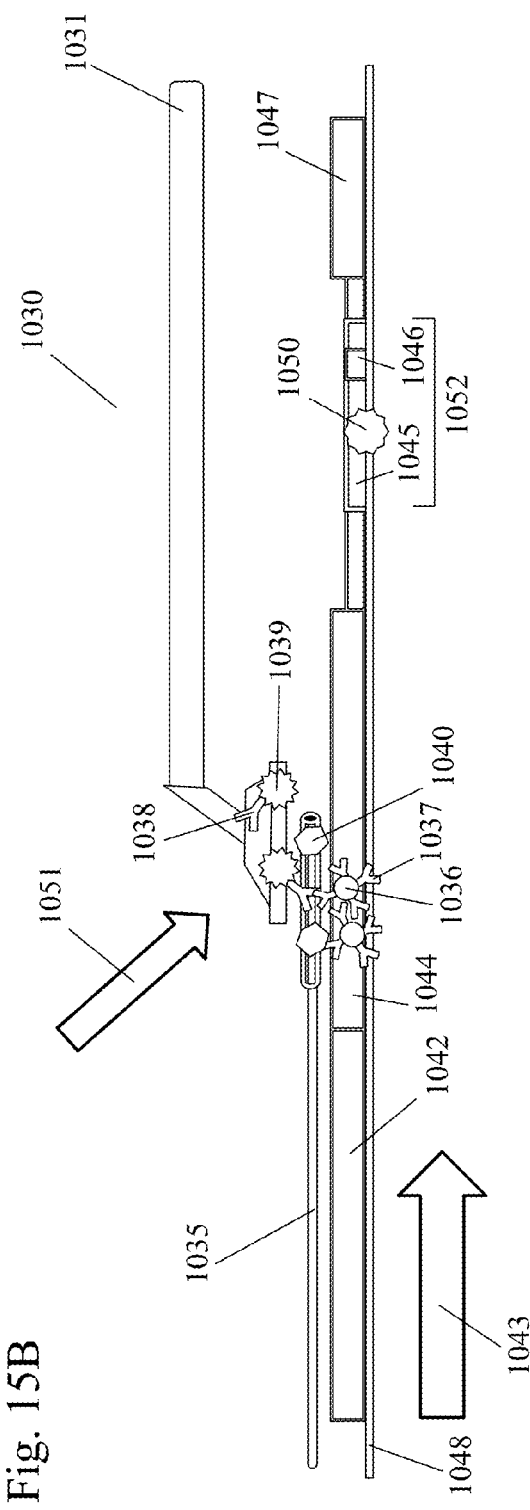
Fig. 15A
Fig. 15B

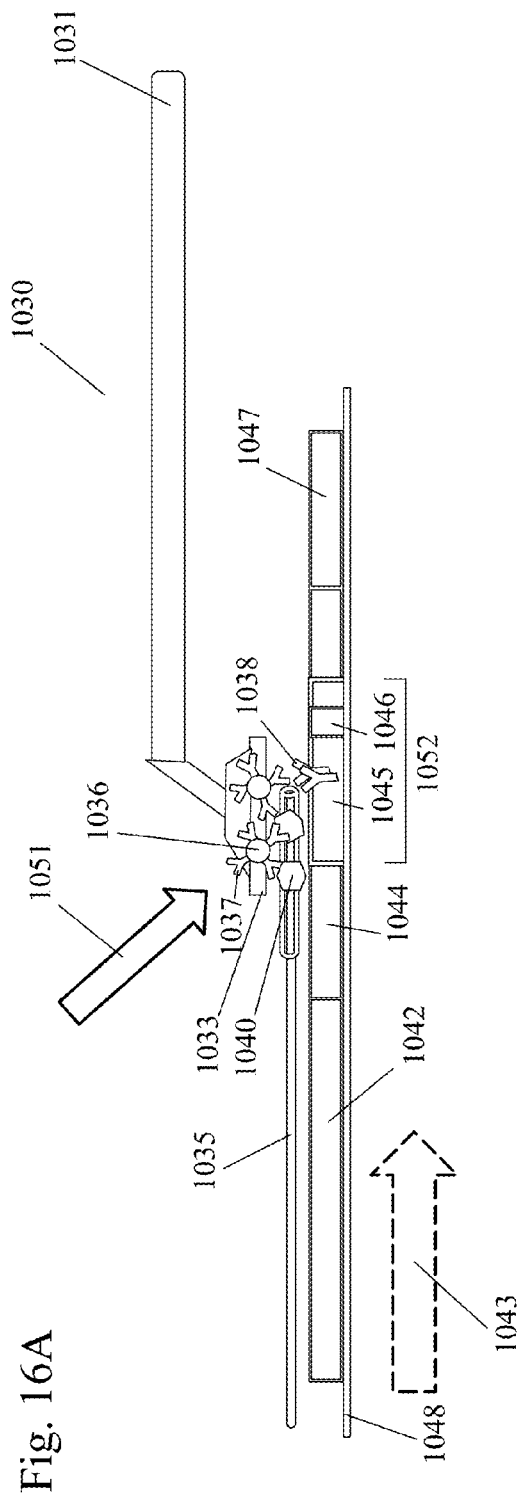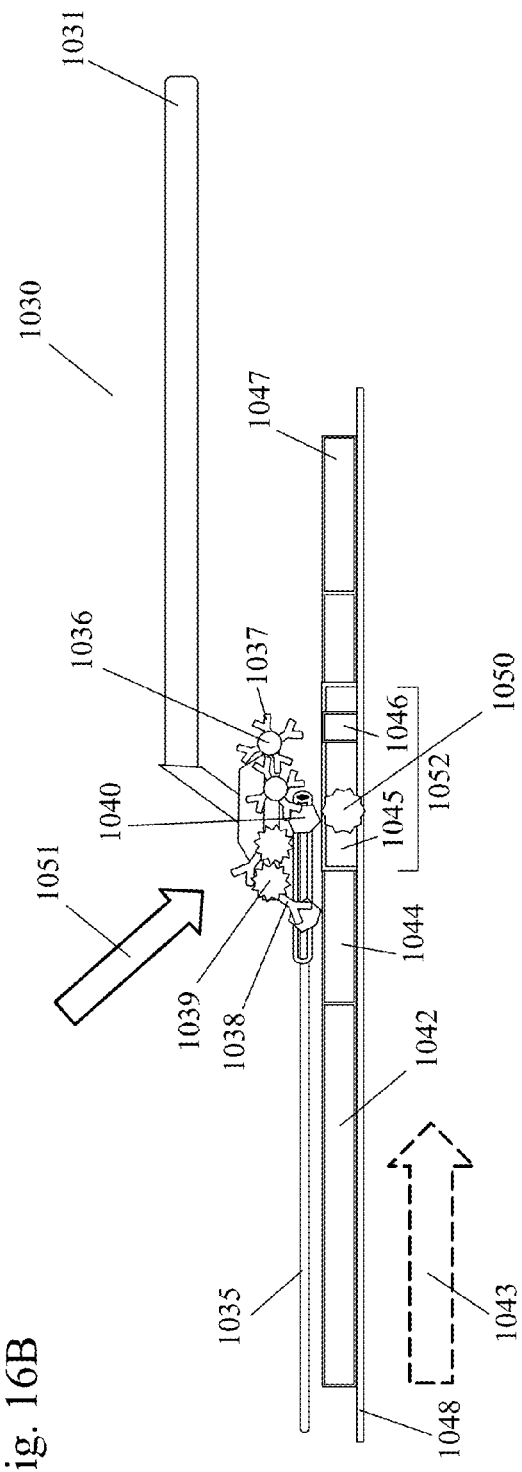

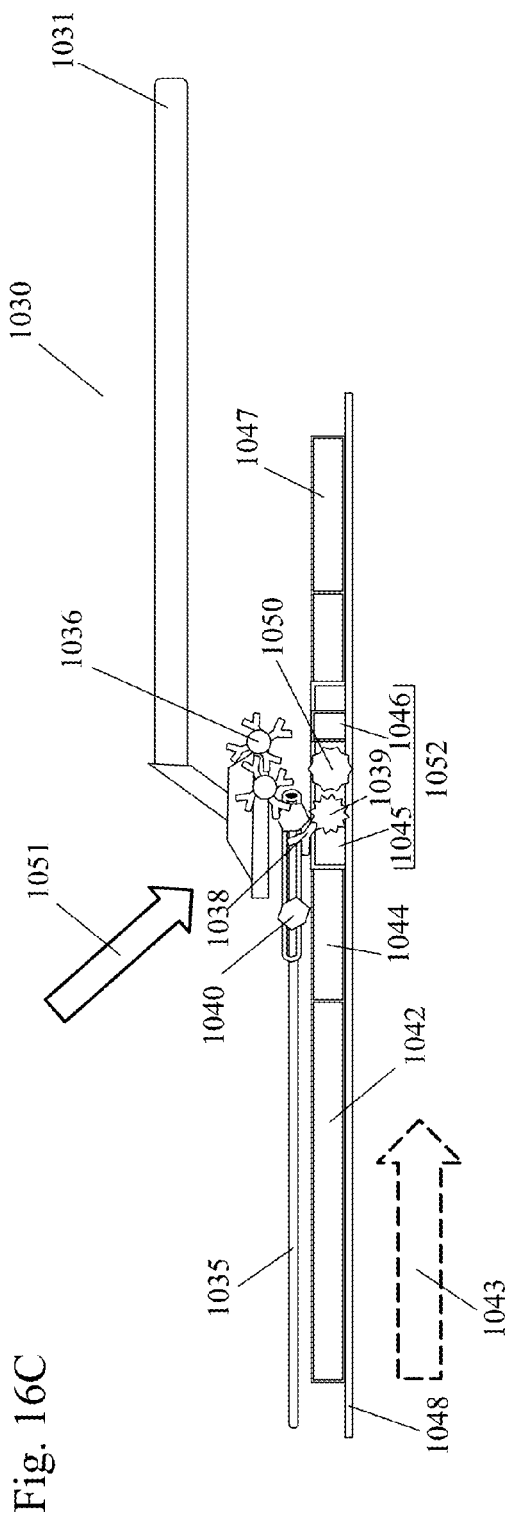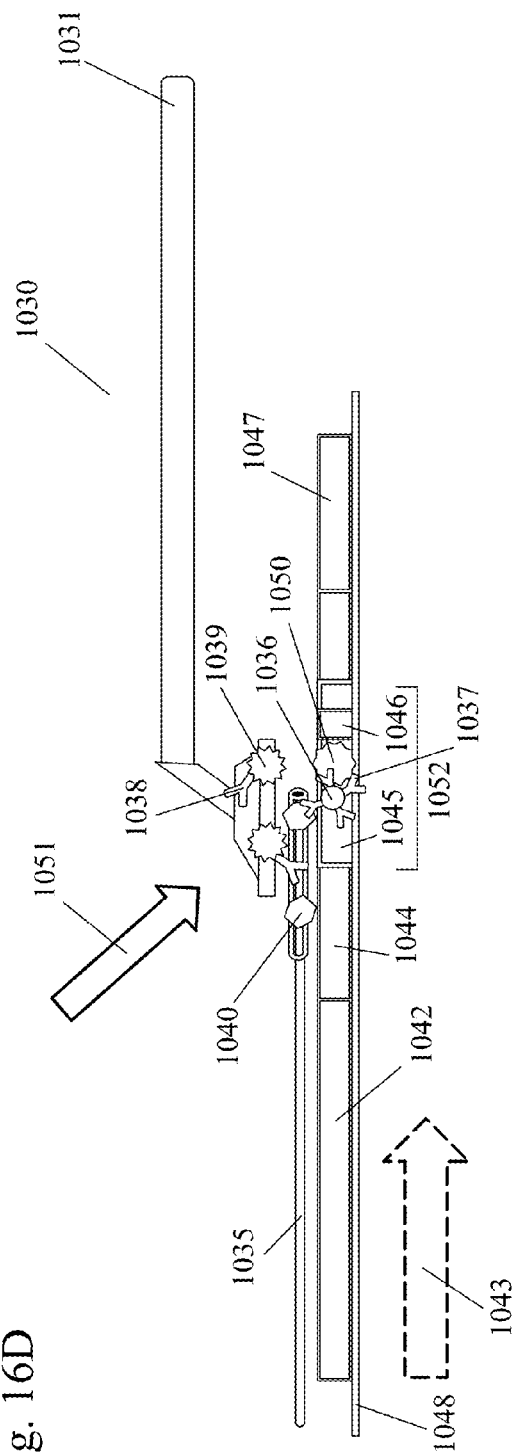
Fig. 16C
Fig. 16D

METHODS AND DEVICES FOR USING MUCOLYTIC AGENTS INCLUDING N-ACETYL CYSTEINE (NAC)

REFERENCE TO RELATED APPLICATIONS

This application is a divisional application of application Ser. No. 13/463,126, filed May 3, 2012, entitled "METHODS AND DEVICES FOR USING MUCOLYTIC AGENTS INCLUDING N-ACETYL CYSTEINE (NAC)", which claims one or more inventions which were disclosed in Provisional Application No. 61/481,907, filed May 3, 2011, entitled "METHODS AND DEVICES FOR USING MUCOLYTIC AGENTS INCLUDING N-ACETYL CYSTEINE (NAC)".

Application Ser. No. 13/463,126 is also a continuation in-part of application Ser. No. 12/502,662, filed Jul. 14, 2009, entitled "IN SITU LYSIS OF CELLS IN LATERAL FLOW IMMUNOASSAYS", now U.S. Pat. No. 8,614,101, issued Dec. 24, 2013, which claims one or more inventions which were disclosed in Provisional Application No. 61/080,879, filed Jul. 15, 2008, entitled "LATERAL FLOW NUCLEIC ACID DETECTOR", Provisional Application No. 61/098,935, filed Sep. 22, 2008, entitled "IN SITU LYSIS OF CELLS IN LATERAL FLOW IMMUNOASSAYS", and Provisional Application No. 61/179,059, filed May 18, 2009, entitled "METHOD AND DEVICE FOR COMBINED DETECTION OF VIRAL AND BACTERIAL INFECTIONS", and which is a continuation-in-part application of application Ser. No. 12/469,207, filed May 20, 2009, entitled "NANOPARTICLES IN DIAGNOSTIC TESTS", which claimed priority from Provisional Application No. 61/071,833, filed May 20, 2008, entitled "NANOPARTICLES IN DIAGNOSTIC TESTS" and application Ser. No. 12/481,631, filed Jun. 10, 2009, entitled "COMBINED VISUAL/FLUORESCENCE ANALYTE DETECTION TEST", now U.S. Pat. No. 8,470,608, issued Jun. 25, 2013, which claimed priority from Provisional Application No. 61/060,258, filed Jun. 10, 2008, entitled "COMBINED VISUAL/FLUORESCENCE ANALYTE DETECTION TEST".

Application Ser. No. 13/463,126 is also a continuation in-part of application Ser. No. 12/958,454, filed Dec. 2, 2010, entitled "MULTIPLANAR LATERAL FLOW ASSAY WITH SAMPLE COMPRESSOR", now U.S. Pat. No. 8,609,433, issued Dec. 17, 2013, which claims one or more inventions which were disclosed in Provisional Application No. 61/266,641, filed Dec. 4, 2009, entitled "LATERAL FLOW NUCLEIC ACID DETECTOR", Provisional Application No. 61/331,966, filed May 6, 2010, entitled "MULTIPLANAR LATERAL FLOW ASSAY WITH SAMPLE COMPRESSOR", Provisional Application No. 61/352,093, filed Jun. 7, 2010, entitled "LATERAL FLOW ASSAYS", and Provisional Application No. 61/392,981, filed Oct. 14, 2010, entitled "MULTIPLANAR LATERAL FLOW ASSAY WITH SAMPLE COMPRESSOR".

The benefit under 35 USC §119(e) of the United States provisional applications is hereby claimed, and the aforementioned applications are hereby incorporated herein by reference.

BACKGROUND OF THE INVENTION

Field of the Invention

The invention pertains to the field of lateral flow assays. More particularly, the invention pertains to in situ lysis and mucolysis of samples in lateral flow assays.

Description of Related Art

Lateral flow immunoassays combine the reagents and the process steps of more general immunoassays into an improved assay. This enables single-step, point-of care testing (POCT) and provides a sensitive and rapid means for detection of target molecules. Lateral flow immunoassays are available for a wide array of target analytes and can be designed for sandwich or competitive test formats. Generally high molecular weight analytes with several epitopes are analyzed in a sandwich format whereas small molecules representing only one epitope are detected by means of a competitive assay. The first lateral flow assays tested for human chorionic gonadotropin (hCG). Today commercially available tests monitor ovulation, detect infectious disease organisms, analyze drugs of abuse and measure other analytes important to human physiology. Products have also been introduced for veterinary testing, environmental testing, and product monitoring.

U.S. Pat. No. 5,714,341 discloses a lateral flow immunoassay for HIV specific antibodies in saliva samples. A saliva sample is diluted in a sample buffer, and a lateral flow immunoassay is dipped into the diluted saliva sample, again enabling point-of-care testing with rapid results.

German Patent DE19622503 discloses a lateral flow immunoassay for illegal narcotics in saliva and sweat.

There is a need for still simpler-to-use and more rapid lateral flow immunoassays suitable for time-sensitive and cost-sensitive clinical settings. This need is most acute in situations where the sample type and target analyte necessitate a sample preparation step. This may occur when an analyte is not readily presented within a sample and a separate lysis step is necessary to free the analyte for efficient presentation. Such an assay may need to directly test for analytes in human body fluids, including analytes which may be protected within complexes or behind membranes including cellular or mucosal membranes.

As an example, fever is a common cause of childhood visits to urgent care centers for both family practice and pediatric offices. Most commonly, this relates to either a respiratory infection or gastroenteritis. The high incidence of fever in children and the precautious administration of unnecessary antibiotics is reason to develop a rapid screening test for biomarkers that distinguish viral from bacterial infections.

The efficiency and even the probability of success of a given immunoassay will depend on the initial presentation of any antigens to be detected. Antigens and other targets must be accessible to antibodies of an assay. Access can be impacted if most or all of the available antigen is masked in a complex or is inaccessible behind a cell membrane, e.g. in a cell's cytoplasm. In these situations, a viable and efficient assay may need to include a lysis step designed to make an antigen accessible, either by breaking up a complex to unmask components or by removing barriers such as a cell wall, a membrane of a cell or organelle, or a coat of a virus. However, such an added lysis step may complicate and delay an assay, even causing it to be too complex or time consuming for practical operation in a clinical setting.

In order to detect analytes protected within a complex of molecules or behind a membrane or other barrier, one approach in the immunoassay field is to lyse the complex or barrier and extract the analyte of interest prior to performing the immunoassay. When the barrier is a cell wall or cell membrane, the cells can be erythrocytes, leukocytes, epidermal, viral, fungal or bacterial, and they can be normal or malignant. Traditionally, a required lysis step is accomplished prior to and physically separate from the desired immunoassay, as a sample preparation step.

Practical operation in point-of care testing means that an assay needs to operate in such a manner as to report a result meeting point-of-care testing requirements including but not limited to timeliness, accuracy, sensitivity, specificity, and ease of use. Therefore, there is a need in the art for methods and devices that can circumvent the need for a separate lysis or mucolysis step prior to running a lateral flow assay.

SUMMARY OF THE INVENTION

Instead of breaking down cells prior to transferring a sample to a point-of-care testing device, the present invention includes devices and methods that incorporate lysis and/or mucolytic agents into a point-of-care testing device so that lysis and/or mucolysis does not need to be conducted as a separate step. The lysis or mucolysis step is performed on the test strip itself, as an integral part of the sample analysis device.

BRIEF DESCRIPTION OF THE DRAWINGS

FIG. 11A shows a lateral flow test strip in an embodiment of the present invention.

FIG. 11C shows a lateral flow device including the test strip of FIG. 11A, a sample collector, and a sample compressor in an embodiment of the present invention.

FIG. 12A shows a lateral flow test strip in an embodiment of the present invention.

FIG. 12B shows a "full" sandwich, which preferably forms before reaching the test line, between the analyte, the labeled conjugate, and a second tagged mobile binding partner.

FIG. 13A shows another lateral flow test strip in an embodiment of the present invention.

FIG. 13C shows a lateral flow device including the test strip of FIG. 13A, a sample collector, and a sample compressor in an embodiment of the present invention.

FIG. 15A shows another lateral flow test strip in an embodiment of the present invention.

FIG. 15B shows a lateral flow device including the test strip of FIG. 15A, a sample collector, and a sample compressor in another embodiment of the present invention.

FIG. 16A shows a device similar to the device of FIG. 11C except that the test zone is located in the sample application zone in an embodiment of the present invention.

FIG. 16B shows a device similar to the device of FIG. 13C except that the test zone is located in the sample application zone in an embodiment of the present invention.

FIG. 16C shows a device similar to the device of FIG. 14B except that the test zone is located in the sample application zone in an embodiment of the present invention.

FIG. 16D shows a device similar to the device of FIG. 15B except that the test zone is located in the sample application zone in an embodiment of the present invention.

DETAILED DESCRIPTION OF THE INVENTION

Figure 1:
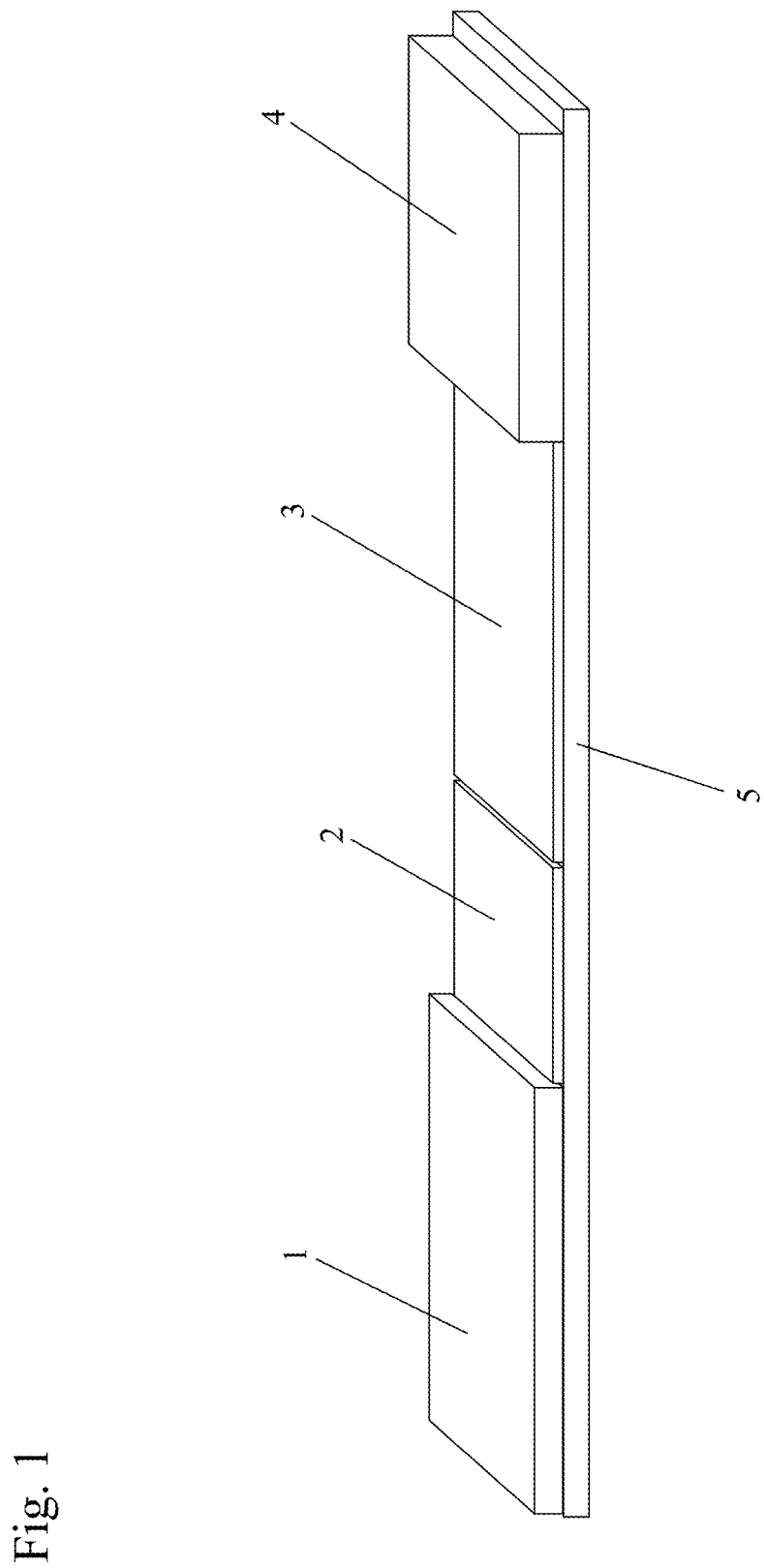
FIG. 1 shows a sample analysis device that may be used in embodiments of the present invention.

Instead of lysing cells or treating a mucosal sample "outside" of a point-of-care testing device, the present invention utilizes "in situ lysis" or "in situ mucolysis". The term "in situ lysis", as used herein, describes techniques for incorporating lysis agents into a point-of-care testing device, such as a chromatography test strip, lateral flow immunoassay device, or other lateral flow device, so that the lysis operation is not conducted as a separate step.

The term "in situ mucolysis" describes techniques for incorporating mucolytic agents into a point-of-care testing device, such as a chromatography test strip, lateral flow immunoassay device, or other lateral flow device. The mucolysis step is not conducted as a separate step.

Mucolytic agents, as defined herein, are agents that reduce the viscosity of mucus, for example by dissolving, digesting, or liquefying the mucus. Mucolysis, as defined herein, is the solution, digestion, or liquefaction of mucus.

Lysis agents, as defined herein, are agents that dissolve or rupture cells, for example by disrupting the cell membrane, whereby intracellular as well as the surface proteins are exposed for better access to the reagents (e.g.—antibodies in immunoassay devices).

In situ lysis and/or mucolysis offer distinct advantages over a separate lysis and/or mucolysis step. Some of these advantages are:

1. Higher efficiency. Cells that are lysed or mucolysed prior to being transferred onto the device would inherently lower the percentage of recovery. Thus, avoiding an additional transfer step promotes efficiency and sensitivity.
2. Higher stability. Many intra-cellular analytes are labile. By greatly reducing the time for interaction with an antibody and antigens in an in situ lysis or mucolysis set up, this lability can be overcome.
3. More rapid testing and results. In situ lysis or mucolysis eliminates the need of separate "outside" lysing or mucolysis steps, thus increasing the rapidity of test results in a point-of-care testing scenario.
4. Reducing interference. With a proper "blocking zone," one can block cell debris or cell bound materials from reaching an assay reaction area. Where an analyte of interest is intra-cellular and a protein associated with a cell wall and other cell debris needs to be blocked, and the assay antibody is protected, then a blocking zone downstream of the lysis and/or mucolytic agent and upstream of an assay readout may be used to decrease interference.

"In situ lysis" and "in situ mucolysis" can also be applied to "breaking down of the complexes," whether they are immune complexes or bound materials of some kind. By lysing or mucolysing these complexes in situ, one can then measure the amount of analyte in the complexes.

In a preferred embodiment, the sample analysis device includes a chromatographic test strip, e.g. a lateral flow or flow through test strip. The test strip includes a sample application zone, a lysis zone and/or a mucolytic zone (this zone may be incorporated into one of the other zones, overlap one of the other zones, or be a completely separate zone), a conjugate zone, and a detection zone. Preferably, the test strip also optionally includes a waste zone, a control zone, a carrier backing, a housing and an opening in the housing for read out of the result. Any combinations of some or all of these elements may be included in the test strip. Sample analysis in the detection zone may be carried out by standard means, e.g. by an immunological, biochemical or enzymatic detection method. Preferably, the detection method includes the use of antibodies, nucleic acids, ligands/receptors or nanoparticles capable of specifically binding the targets, e.g. pathogens to be tested and subsequent visualization of the bound entity, e.g. by enzymatic detection or by means of direct labeling groups, such as visible or colored particles, dyes, magnetic particles, fluorescent or phosphorescent particles, chemiluminiscent particles, radioisotopic ligands, enzymes, peptides, amino acids, colloidal particles, or beads, as is well known in the art.

Detection of the marker may be achieved in the detection zone. The binding molecule immobilizes the labeled complex or the labeled marker-analogue by immune reaction or other reaction in the detection zone, thus building up a visible test line in the detection zone during the process. Preferably, the label is an optically detectable label. Forming a complex at the test line concentrates and immobilizes the label and the test line becomes visible to the naked eye, indicating a positive test result. Particularly preferred are direct labels, and more particularly gold labels which can be best recognized by the naked eye. Additionally, an electronic read out device (e.g. on the basis of a photometrical, acoustic, impedimetrical, potentiometric and/or amperometric transducer) can be used to obtain more precise results and a semi-quantification of the analyte. Other labels may be latex, fluorophores, or phosphorophores.

Furthermore, this invention includes a device and test kit for the performance of the described method.

In some preferred embodiments, the specific binding partners for the analytes in the sample are monoclonal, polyclonal, single domain or recombinant antibodies, or fragments of antibodies capable of binding to a pathogen. Alternatively, the specific binding partners may also be antigens capable of binding to antibodies against a pathogen or an allergen. Other types of binding partners include, but are not limited to, bioorganic macromolecules like aptamers or ligands/receptors, nanoparticles, or nucleic acids.

The visual label may be any label visible to the naked eye, including, but not limited to, colored particles such as colloidal gold, dyed latex beads, selenium, or carbon. In some embodiments, the visual tags are also coated with fluorescing elements. In some embodiments, the fluorescing element is a fluorescing dye. Alternatively, a mixture of preferably colorless fluorescing latex bead conjugates are mixed with colloidal gold (a visible spectrum) conjugates, or conjugates producing a visible read test line, in lateral flow assays to enhance sensitivity of the assay and to aid in visually reading true positives and true negatives. In embodiments where nanoparticles are used, the nanoparticles that may be used include, but are not limited to, selenium, carbon, and colloidal gold.

Preferred targets include, but are not limited to, proteins, glycoproteins, proteoglycans, nucleic acids, and lipoproteins. Other preferred targets include, but are not limited to, pathogens, low-molecular-weight compounds, and/or allergy-associated components. The pathogens are preferably selected from viruses, microorganisms, e.g. bacteria, and parasites, e.g. amoebae or nematodes. The allergy-associated components are preferably selected from allergens and anti-allergic components.

In some preferred embodiments, the sample is a sample of body fluid. In these embodiments, the sample of body fluid is preferably taken from a body surface selected from mucosal membrane fluids (preferably of the oral, nasal, vaginal, and ocular cavities), blood, urine, tears, cerebrospinal fluid, secretions from glands and secretions from lesions or blisters, e.g. lesions or blisters on the skin. More preferably, the sample is selected from oral, nasal, ocular, genital and rectal fluid, secretions from skin lesions or blisters, CSF (cerebral spinal fluid), and exudates. In some embodiments, the body fluid samples are preferably fluids that do not flow once collected.

In embodiments where mucosal membrane fluids are used, at least one mucolytic agent is preferably used to breakdown the mucus and make the target more accessible for testing.

Lateral flow devices are known, and are described in, e.g., U.S. Published Patent Application Nos. 2005/0175992 and 2007/0059682. The contents of both of these applications are incorporated herein by reference. Other lateral flow devices known in the art could alternatively be used with the systems and methods of the present invention.

U.S. Published Patent Application No. 2007/0059682, discloses detecting an analyte and a sample which can also contain one or more interfering substances. This publication teaches separating the analyte from the interfering substances by capturing the interfering substances on the chromatographic carrier, and detecting the analyte on the carrier separated from the interfering substances.

U.S. Published Patent Application No. 2005/0175992 discloses a method for detecting targets, such as pathogens and/or allergy-associated components, in a human body fluid where the body fluid sample is collected by a collection device, such as a swab member. The samples are transferred from the swab member to a sample analysis device, on which an analysis of the targets can occur by immunochemical or enzymatic means. The test result is capable of being displayed within a very short period of time and can be directly read out by the user. This enables point-of-care testing with results available during a patient visit. The inventions disclosed in this application are particularly advantageous for the diagnosis of conjunctivitis.

The chromatographic test strip shown in FIGS. 1 through 4 includes a plurality of different strip materials. The device preferably includes an absorbent pad 1, an application zone 2, a detection zone 3, and a waste zone 4. The strip materials are arranged on an adhesive plastic backing 5. The absorbent pad 1 is provided in this example for adding an elution medium in order to facilitate the transfer of the sample to the detection zone 3. US Published Patent Application No. 2007/0059682, describes methods to increase specificity of lateral flow immunoassays. These methods could also be used in combination with the embodiments described herein.

Figure 2:
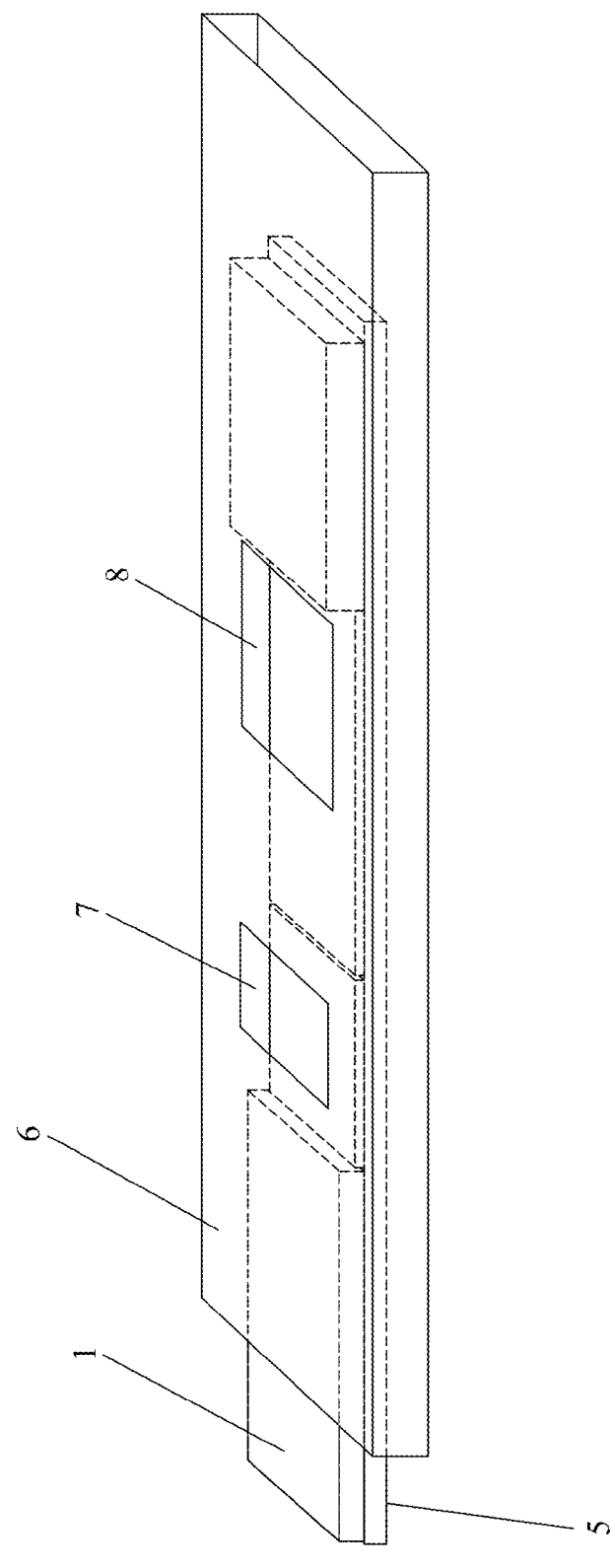
FIG. 2 shows a housing containing the strip of FIG. 1.
Figure 3:
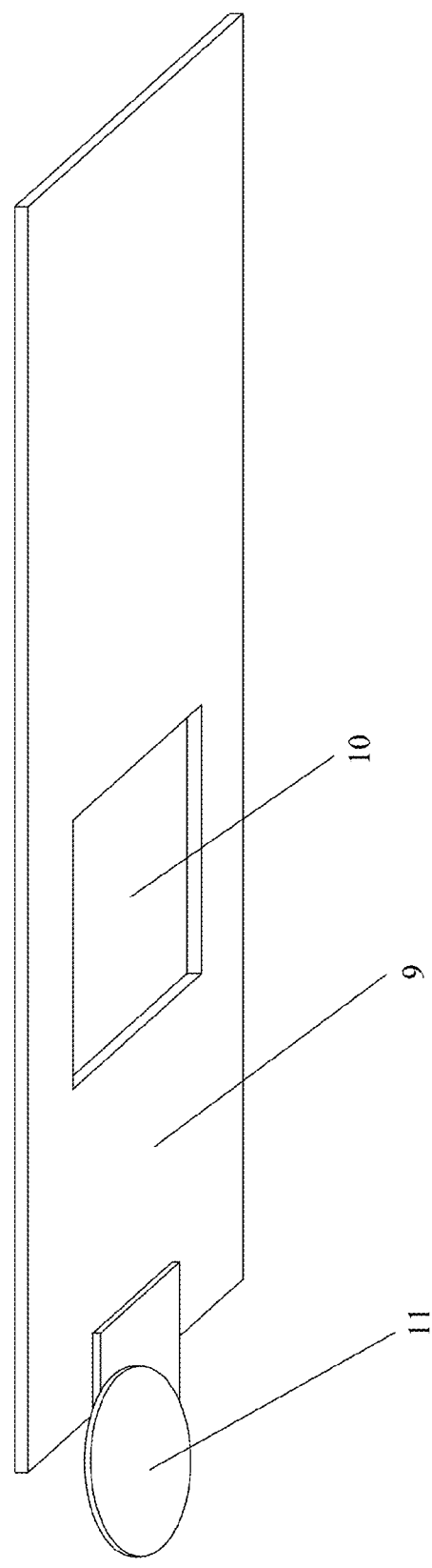
FIG. 3 shows a collection device for collecting a sample.
Figure 4:
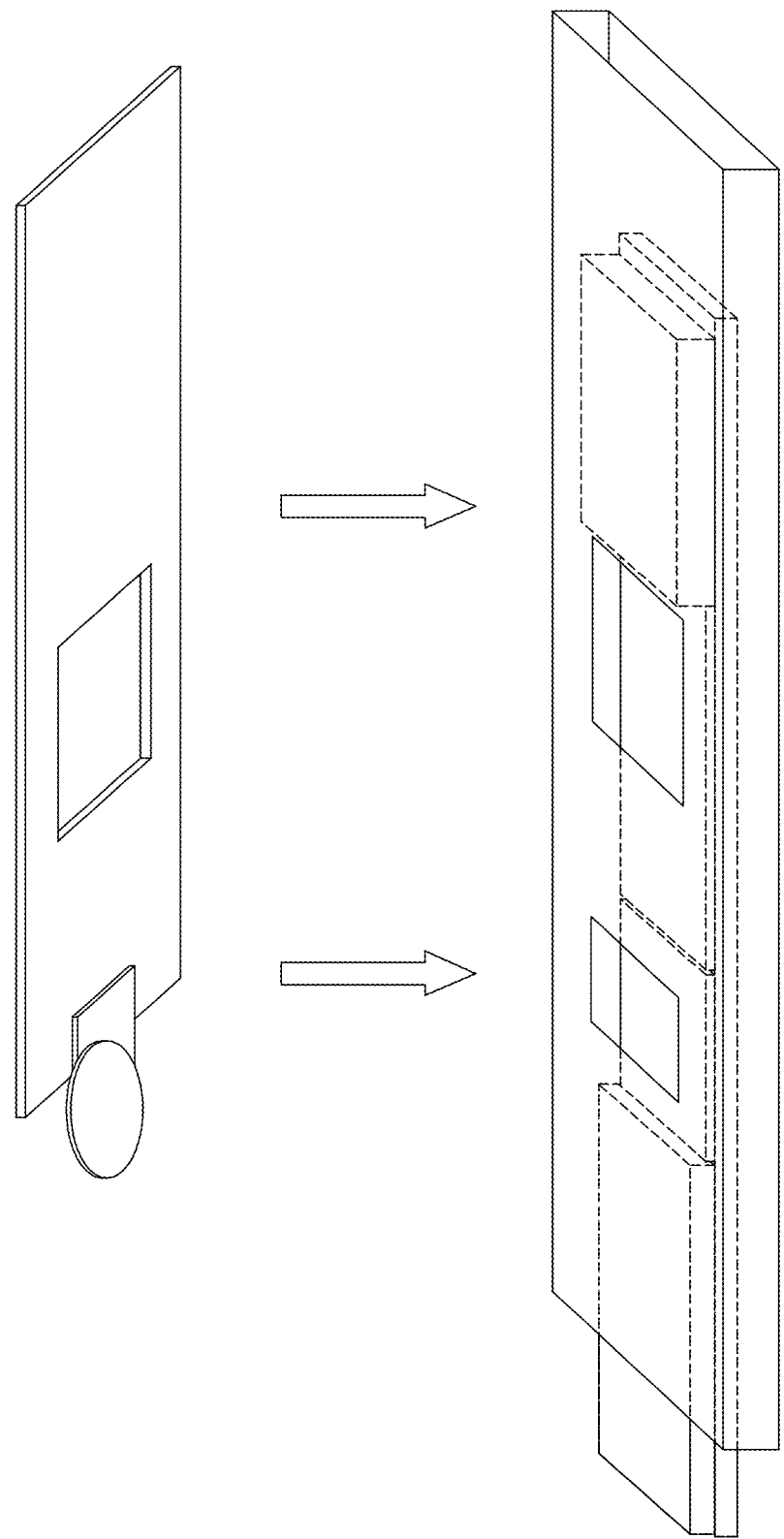
FIG. 4 shows a test kit including the sample analysis device of FIGS. 1 and 2 and the collection device of FIG. 3.

FIG. 2 shows a housing 6, which is preferably plastic, containing the strip as shown in FIG. 1. A sample application window 7 brings a collection device into contact with the strip. The test result is displayed in the read out window 8. FIG. 3 shows the collection device for collecting a sample. In one example, the collection device is a swab member. The collection device includes a body 9, which is preferably plastic, with a sample collection material 11 fixed on it and an opening 10 corresponding to a read out window when the collection device is operatively in contact with a test strip. FIG. 4 shows a test kit, which includes the sample analysis device of FIGS. 1 and 2 and the collection device of FIG. 3.

The methods and devices of the present invention incorporate a lysis zone including at least one lysis agent, and/or a mucolysis zone including at least one mucolytic agent, as part of a lateral flow test strip, such as those shown in FIGS. 1 through 4, or other lateral flow devices known in the art, in order to break down the sample material in situ.

The present invention is suitable for various methods for loading the sample. The assay will either be started directly when sample is transferred in a sufficient volume of liquid, such as a body fluid, or the process may require that a sample be added to or eluted by a sample transport liquid (e.g. tap water or a buffer solution). In one preferred embodiment, a sample which has been collected, such as by a swab, is transferred directly onto the sample application zone of a test strip. In this embodiment, a sample transport liquid is then added to the test strip. In another preferred embodiment, a liquid sample is deposited directly onto the sample application zone of a test strip. In this embodiment, the liquid sample itself, if of sufficient volume, becomes the transport liquid. If the volume of the liquid sample is insufficient, then a sample transport liquid is additionally added. In yet another preferred embodiment, a liquid sample is pre-mixed with the sample transport liquid and then both are applied to the test strip together.

Following sample loading, sample traveling with the transport liquid will encounter one or more lysis agents and/or one or more mucolytic agents. The lysis or mucolytic agent agent will have been pre-loaded onto the test strip and is eluted by the transport liquid. In some preferred embodiments the lysis or mucolytic agent has been dried into the test strip. Alternatively, the lysis or mucolytic agent may be pre-dried by freeze drying or lyophilizing and then pre-loaded into the test strip. In other embodiments, the lysis agent or the mucolytic agent may be absorbed, adsorbed, embedded or trapped on the test strip. In a preferred embodiment, the lysis agent or the mucolytic agent is localized between the sample application zone and the conjugate zone. The lysis agent or the mucolytic agent is preferably soluble or miscible in the sample transport liquid, and the lysis agent or mucolytic agent is solubilized and activated upon contact with the sample transport liquid. The sample transport liquid then contains both lysis and/or mucolytic agent (in solution or suspension) and sample components (in suspension). Any lysis-susceptible or mucolysis-susceptible components in the sample, then being exposed in suspension to the lysis agent and/or the mucolytic agent, are themselves lysed or mucolysed in situ. The running buffer then carries the analyte, including any lysis or mucolysis-freed components, through the conjugate zone and to the detection zone.

The location where the lysis agent and/or the mucolytic agent is pre-loaded can be varied as needed. In order to maximize the time that the sample has to interact with the lysis or mucolytic agent as well as to minimize the amount of lysis or mucolytic agent reaching the detection zone, the dried, absorbed, adsorbed, embedded, or trapped lysis or mucolytic agent may be located in or just downstream of the sample application zone. Or, in order to minimize the distance in which the lysed or mucolysed product must travel before reaching the conjugate zone, the lysis or mucolytic agent may be located closer to the conjugate zone.

In some preferred embodiments, more than one lysis agent, more than one mucolytic agent, or a combination of one or more lysis agents and one or more mucolytic agents may be used.

The concentration of lysis agent pre-loaded onto a test strip is preferably between 0.001% and 5% weight/volume. The volume to be pre-loaded depends on where the lysis agent is pre-loaded. Appropriate ranges are 1 to 10 microliters when pre-loaded into the sample collector fleece (the sample application zone) or 5 to 50 microliters when pre-loaded into the absorbent pad or into other locations within the test strip. Ideally, the amount pre-loaded should be approximately 3 microliters pre-loaded into the sample collector fleece or approximately 10 microliters pre-loaded into the absorbent pad or into other locations within the test strip.

The concentration of mucolytic agents pre-loaded onto a test strip is preferably between 0.01% and 10% weight/volume (or between 0.01% and 10% volume/volume). Similar to the discussion above with respect to lysis agents, the volume of the mucolytic agent to be pre-loaded depends on where the mucolytic agent is pre-loaded.

Selection of a specific lysing environment and agent will depend on the analyte and the assay. pH and ionic strength are key to the lysing environment. As to pH established by the lysis agent, a pH below 4.0 tends to precipitate materials, especially proteins. Higher pH, above approximately 10.0, tends to lyse materials such as proteins and cells walls. Therefore, a pH of approximately 10.0 or above is preferable for many applications. Alternatively, lower pH may be preferred for nucleic acid targets. Similar considerations can be considered when selecting a specific mucolytic environment.

As to ionic strength established by the lysis agent, both high and low ionic strength may be used to lyse. For example, a lower ionic strength (hypotonic) tends to break up erythrocytes. Water by itself can lyse erythrocytes. Higher ionic strength environments may be used to rupture certain cell walls and membranes.

As to specific lysis agents, they may be grouped and selected based on their properties: salts, amphoteric and cationic agents, ionic and non-ionic detergents. The salt, Ammonium Chloride ($NH_4Cl$), lyses erythrocytes. Other salts, including, but not limited to, high concentrations of Sodium Chloride (NaCl) and Potassium Chloride (KCl), may rupture certain cell walls and membranes. Other lysis agents are amphoteric agents including, but not limited to, Lyso PC, CHAPS, and Zwittergent. Alternatively, cationic agents including, but not limited to, C16 TAB and Benzalkonium Chloride may be used as a lysis agent. Both ionic and non-ionic detergents are often used to break or lyse the cell wall or cell membrane components such as lipoproteins and glycoproteins. Common ionic detergents include, but are not limited to, SDS, Cholate, and Deoxycholate. Ionic detergents are good solubilizing agents. Antibodies retain their activity in 0.1% SDS or less. Common non-ionic detergents include, but are not limited to, Octylglucoside, Digitonin, C12E8, Lubrol, Triton X-100, Noniodet P-40, Tween 20, and Tween 80. Non-ionic and mild ionic detergents are weaker denaturants and often are used to solubilize membrane proteins such as viral surface proteins. Additional lysis agents include, but are not limited to, urea and enzymes. Combinations of different lysis agents may be used to optimize the lysing environment.

Surfactants are generally wetting agents and lower the surface tension of a liquid. This then allows easier spreading by lowering the interfacial tension between liquids. So, surfactants can interfere with the natural binding of antigen and antibody or ligand and receptors. The concentrations are, therefore, experimentally chosen for each class of lysis agent. Once lysis occurs, it is important that the desired binding reactions not be hindered. Generally, 0.001% lysis agent concentration is considered the lower limit, and the upper limit is approximately 1%. There is an additive or synergistic effect when combinations of lysis agents are used. This expands the working range of concentration to run from approximately 0.001% to 1%. Finally, some undesirable non-specific binding may be prevented at a Tween 20 concentration of 5%. In all cases, the total amount of lysis agent pre-loaded onto all locations of an individual test strip must be sufficient to lyse barriers to immunodetection, permitting practical operation of the test strip.

Any mucolytic agent capable of effectively degrading the mucus in the sample could be used. Some examples for mucolytic agents include proteolytic enzymes including, but not limited to, Lysozyme, Trypsin and Chymotrypsin. Lipases and Nucleases can also be used alone or in combination. In certain applications, chaotropic agents and chelating agents such as EDTA can also be used. Some specific examples include, but are not limited to, N-acetyl cysteine (NAC, aka N-acetyl-L Cysteine), Acetylcysteine, Ambroxol, Bromhexine, Carbocisteine, Domiodol, Dornase alpha, Eprazinone, Erdosteine, Guiafenesin Letosteine, Mesna (2-MercaptoEthane Sulfonate sodium), Neltenexine, Sobrerol, Stepronin, and Tiopronin.

In a preferred embodiment, NAC is used. NAC has many properties that make it an ideal mucolytic agent for in situ mucolysis in point of care assays. NAC is soluble in both aqueous and non-aqueous solutions. The solubility and the toxicity of NAC are irrelevant at the levels needed for mucolysis on chromatographic test strips. In a preferred embodiment, the amount of NAC in the solution ranges from approximately 0.01 to 10% of the total volume (weight/volume or volume/volume) of the solution. NAC is known to be bio-compatible so it can be used even on sample collection materials that come in direct contact with bodily fluids. NAC cannot be immobilized on the nitrocellulose since it is not a protein but is a modified amino acid. The SH group on NAC confers the mucolytic activity of NAC and the SH group on NAC is the preferred moiety for passive conjugation to colloidal gold. The SH group on NAC also makes it suitable for "directional" chemical binding to microspheres such as latex beads. NAC is stable in dried form as well as in buffers. NAC should be thermally stable or unaffected by Ethylene Oxide (EtO) and hence, can remain active on a test strip after sterilization of the test strip with NAC on it.

In another preferred embodiment, a modified form of Acetyl cysteine could be used as the mucolytic agent. In its modified form, the Acetyl group goes on the Cysteine moiety not through the $NH_2$ end as in n-Acetyl Cysteine but goes on to the Cysteine moiety through the Beta Carbon's $CH_3$ group.

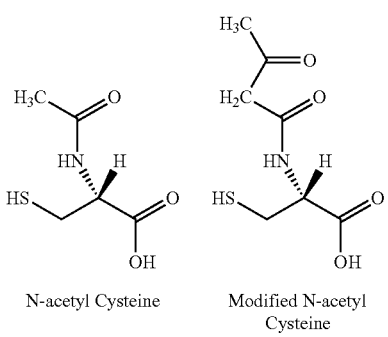

N-acetyl Cysteine    Modified N-acetyl Cysteine

The lysis agent or mucolytic agent itself preferably does not interfere with any other assay detector or indicator agents and thus does not interfere with any other assay interactions and reactions to such an extent as to prevent practical operation of the assay. A lysis agent or mucolytic agent should have sufficient shelf life to allow manufacture, distribution and storage before use of a test strip in point-of-care testing.

In a preferred embodiment of the present invention, the lateral flow assay device of the present invention includes a sample-transporting liquid, which can be a buffer, and a chromatography test strip containing one or several fleece materials or membranes with capillary properties through which sample flows. In a device and method of the invention, it is unnecessary to lyse the cells in the sample prior to applying it to the test strip.

In a preferred embodiment, as shown in FIGS. 5A through 5D, the sample is applied to the application zone 201 on a chromatography test strip 200. The sample passes a lysis zone 250, where a lysis agent will have preferably been pre-loaded onto the test strip and is eluted by the transport liquid. The lysis agent lyses any lysis-susceptible components in the sample in situ.

The chromatographic test strip contains a sample application zone 201, a lysis zone 250 containing a lysis agent, and a conjugate zone 260 containing at least one labeled binding partner that is eluted by and then able to migrate with a sample transport liquid (e.g. a buffer solution). The labeled binding partner is capable of specifically binding to an analyte of interest to form a conjugate which in turn is capable of specifically binding to another specific reagent or binding partner in the detection zone. Although not shown in these Figures, an absorbent pad, similar to the absorbent pad 1 shown in FIG. 1, as well as other known lateral flow assay components including, but not limited to, a waste zone, a carrier backing, a housing and an opening in the housing for result read out may optionally also be a component of the test strip 200 in this embodiment.

In a preferred embodiment, the lysis agent is localized in the lysis zone 250 between the sample application zone 201 and the conjugate zone 260. The lysis agent is preferably soluble or miscible in the sample transport liquid, and the lysis agent is solubilized and activated upon contact with the sample transport liquid. The sample transport liquid then contains both lysis agent in solution or suspension and sample components in suspension. Any lysis-susceptible components in a sample, then being exposed in suspension to the lysis agent, are themselves lysed in situ. The running buffer then carries the analyte, including any lysis-freed components, to the detection zone 205.

Figure 5A:
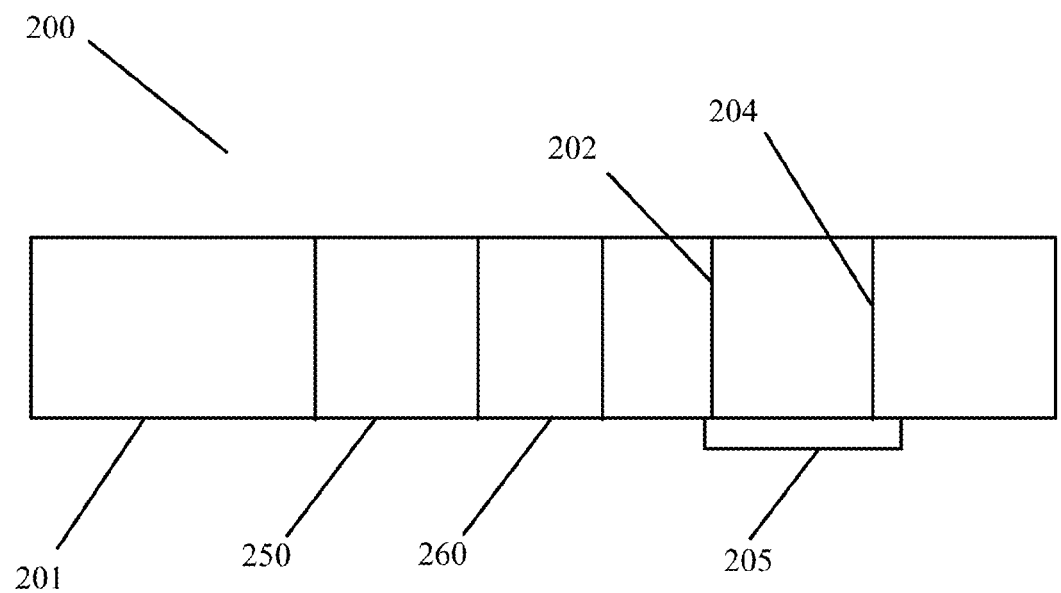
FIG. 5A shows a sample analysis device including a lysis zone located between a sample application zone and a conjugate zone in an embodiment of the present invention.
Figure 5B:
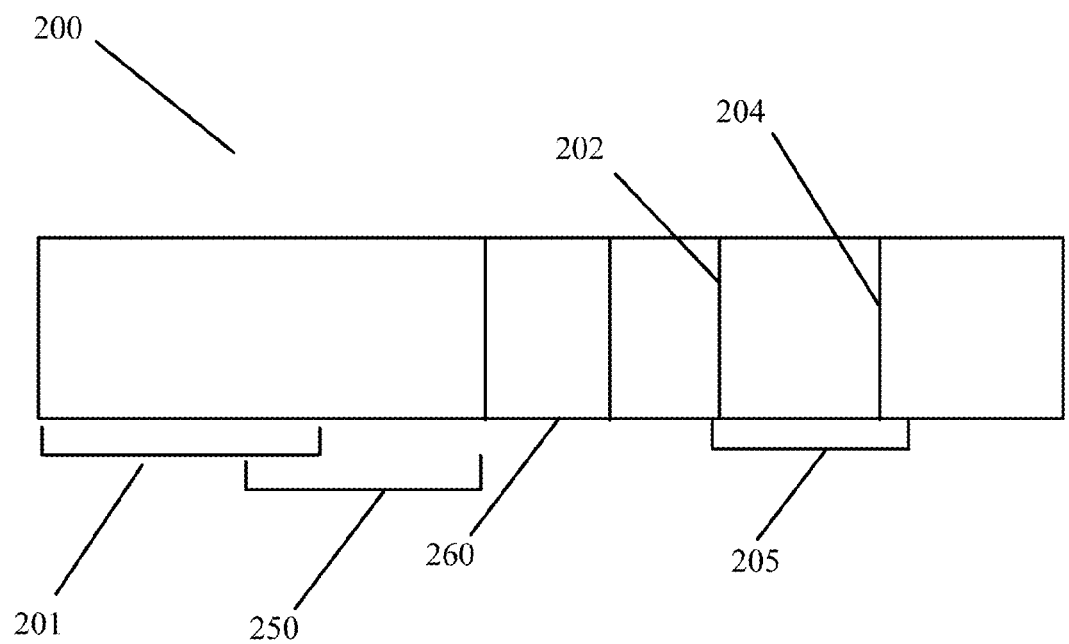
FIG. 5B shows a sample analysis device including a lysis zone overlapping a sample application zone in an embodiment of the present invention.
Figure 5C:
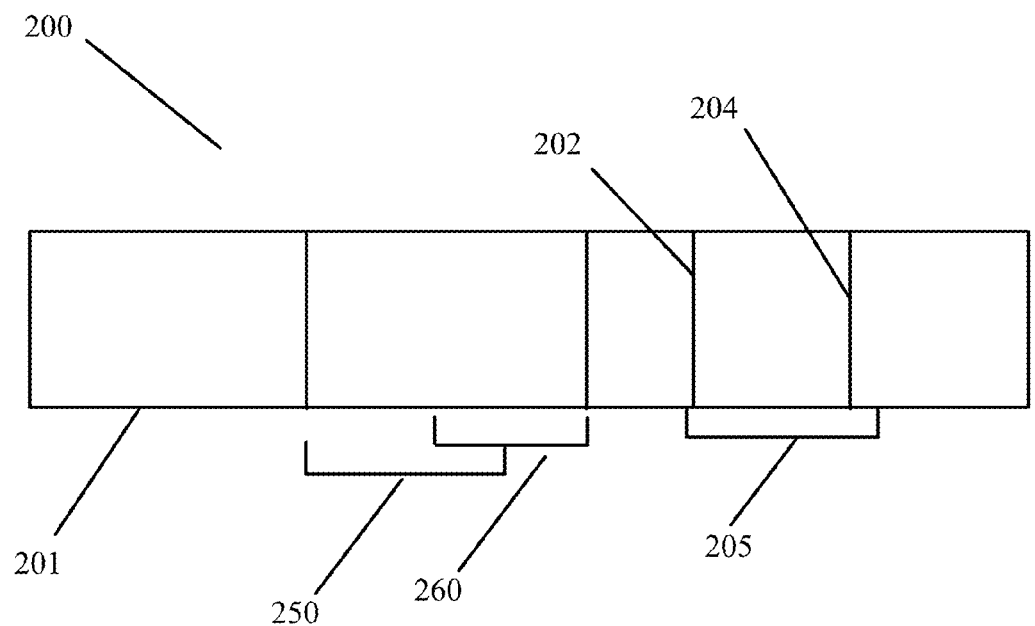
FIG. 5C shows a sample analysis device including a lysis zone overlapping a conjugate zone in an embodiment of the present invention.
Figure 5D:
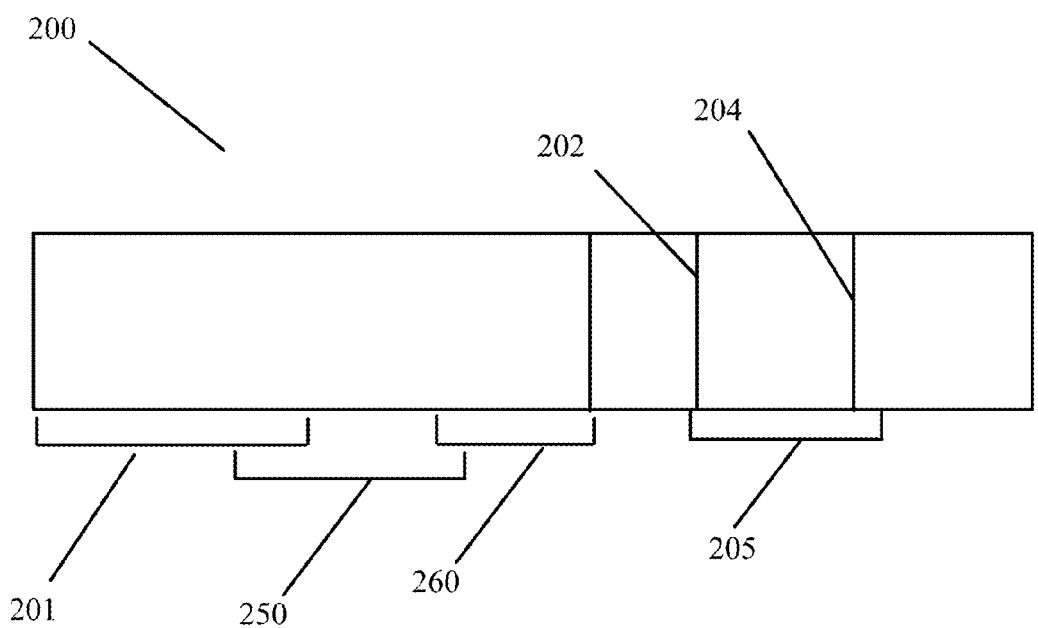
FIG. 5D shows a sample analysis device including a lysis zone overlapping a sample application zone and a conjugate zone in an embodiment of the present invention.
Figure 6A:
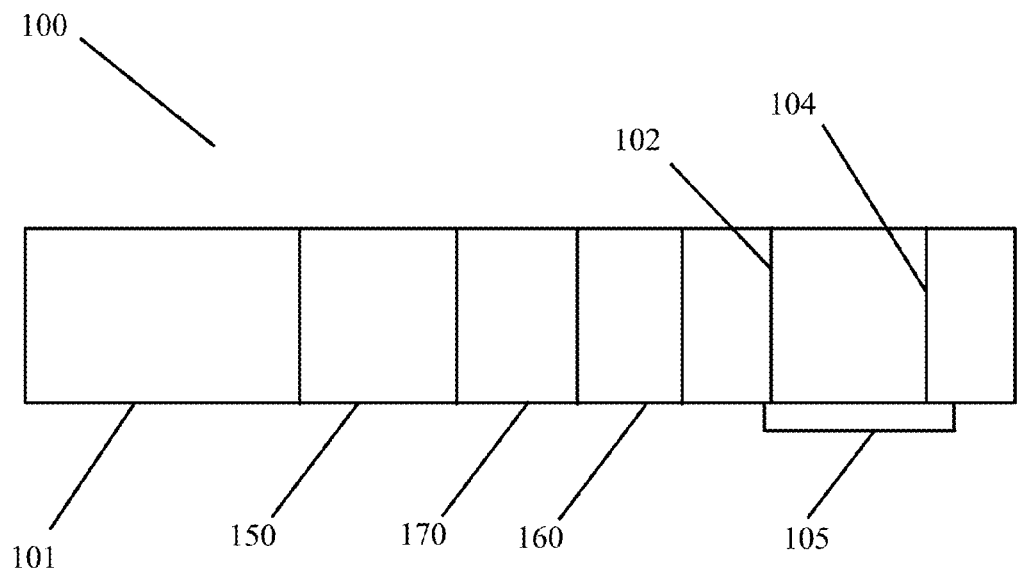
FIG. 6A shows a sample analysis device including a blocking zone between a sample application zone and a conjugate zone in an embodiment of the present invention.
Figure 6B:
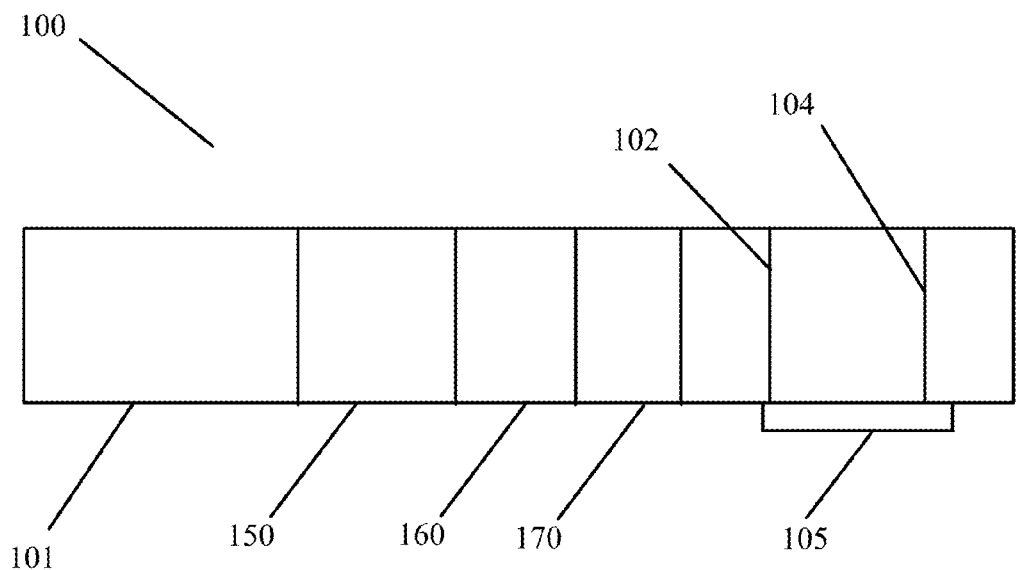
FIG. 6B shows a sample analysis device including a blocking zone between a sample application zone and a detection zone in another embodiment of the present invention.
Figure 6C:
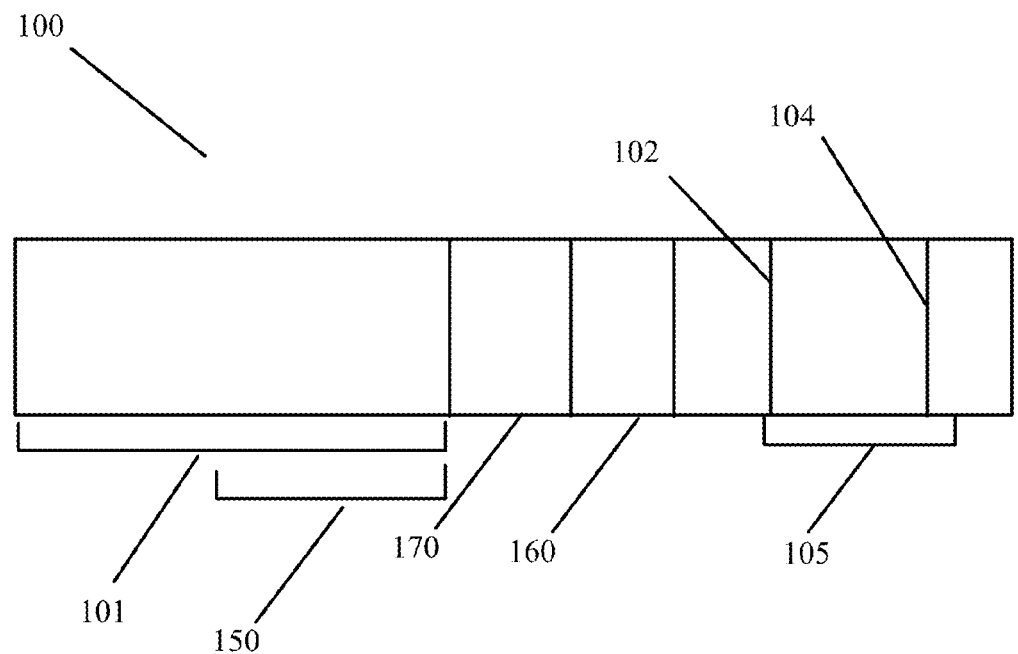
FIG. 6C shows a sample analysis device including a blocking zone between a sample application zone and a conjugate zone in another embodiment of the present invention.
Figure 6D:
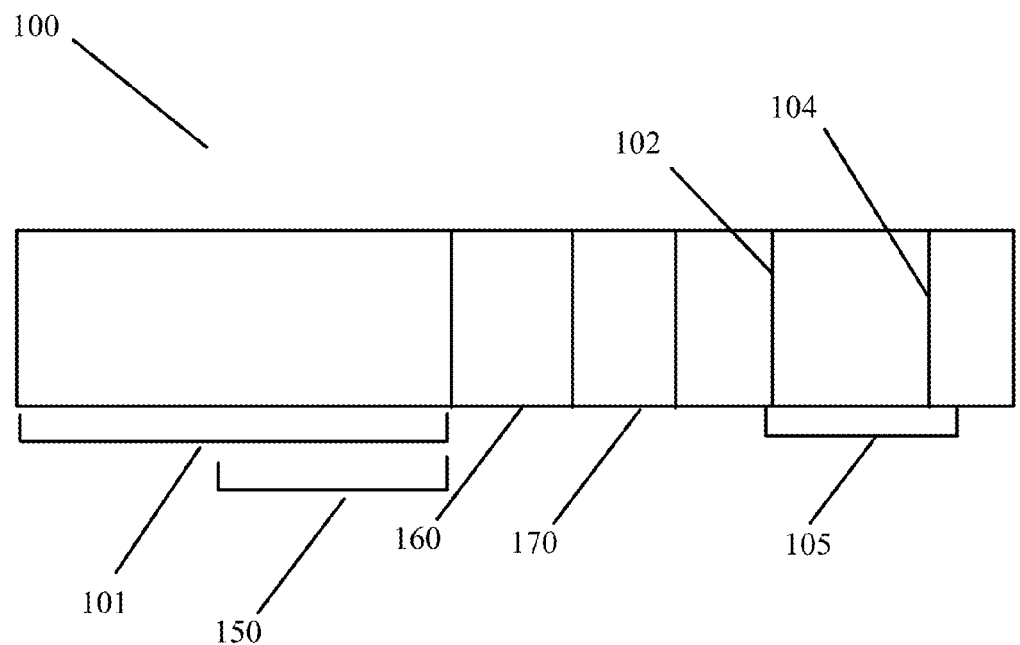
FIG. 6D shows a sample analysis device including a blocking zone between a sample application zone and a detection zone in another embodiment of the present invention

The lysis zone 250 is preferably located between the sample application zone 201 and the conjugate zone 260, as shown in FIG. 5A. In other embodiments, the lysis zone 250 overlaps the sample application zone 201, the conjugate zone 260 or both the sample application zone 201 and the conjugate zone 260 as shown in FIGS. 5B, 5C, and 5D, respectively. Note that the figures are schematic, and are not drawn to scale. The amount of overlap between the different zones (as shown in FIGS. 5B through 5D) may be highly variable.

The test strip 200 also includes a detection zone 205 containing a first section for detection of a first analyte, e.g. a test line 202, including an immobilized specific binding partner, complimentary to the conjugate formed in and arriving from the conjugate zone (260). Thus, at the test line 202, detection zone binding partners trap the labeled binding partners from the conjugate zone 260 along with their bound analytes. This localization of the analytes with their labeled binding partners gives rise to an indication at the test line 202. At the test line 202, the presence of an analyte is determined by qualitative and/or quantitative readout of the test line 202 indication resulting from the accumulation of labeled binding partners. Optionally, the detection zone 205 may contain further test lines to detect other analytes, as well as a control line 204. The control line 204 indicates that the labeled specific binding partner traveled through the length of the assay, even though it may not have bound any analyte, thus confirming proper operation of the assay. As shown in FIGS. 5A through 5D, the control zone 204 is preferably downstream of the test zone 202. However, in other embodiments, the control zone 204 may be located upstream of the test zone 202.

In a preferred embodiment, the control line 204 includes an antibody or other recombinant protein which binds to a component of the elution medium or other composition being used in the test. In embodiments where nucleic acids are the targets, the control line (204) preferably includes a nucleic acid complementary to the labeled nucleic acid being used as a binding partner for the target nucleic acid.

Although only one test line is shown in the figures, multiple test lines are within the spirit of the invention. In some embodiments where there are multiple targets, the presence of each target preferably corresponds to a separate test line 202. In other embodiments where there are multiple targets, the presence of multiple targets may be indicated on the same test line such that the presence of more than one target has different characteristics than the presence of a single target. For example, the presence of multiple targets on the same test line may be visually indicated by a different color than the presence of each of the targets alone.

In other embodiments, it is possible to have one or more mild lysis agents in the running buffer itself. In these embodiments, there is no adverse effect on the conjugate zone which will be downstream and the sample can either be upstream or downstream of the conjugate zone. A lysing enzyme in the running buffer can "target" its substrate and cut it to open up the cell wall. As an example, penicillin can excise or "punch a hole" in a susceptible bacteria. In other embodiments, when the lysis agent is applied to the sample collection material 11 (see FIG. 3), then the conjugate zone may be upstream of the sample application zone.

In another preferred embodiment, a barrier may be disposed in a "blocking zone" between the sample application zone and either the conjugate zone or the detection zone, preferably before the conjugate zone. In this case, the lysis agent is pre-loaded in the sample application zone or between the sample application zone and the barrier. Thus, lysis occurs before the sample reaches the barrier, and the barrier serves to slow or arrest those lysed materials effectively larger than the porosity of the barrier while permitting effectively smaller materials to pass more easily. Thus, the barrier provides a filtering effect and reduces interference with binding interactions in the conjugate and detection zones. Selection of a specific barrier material depends on the analyte and the assay.

A blocking zone barrier may be physical or biological. Examples of physical barriers include glass fiber matrices which inherently bind or trap erythrocytes and their cellular debris. Other physical matrices may be "sieve-type" matrices, as in a filtering system, where the small pore size blocks passage of cells but does allow passage of biomarkers.

In contrast, biological barriers are immobilized biological materials that specifically bind to ligands or receptors on a cell surface, preventing the cells from flowing further. Examples include antibodies, recombinant proteins, specific lectins, and receptors/ligands. Biological materials may also be combined into physical barriers such as glass fiber membranes.

FIGS. 6A through 6D show a barrier disposed in a "blocking zone" 170 between the sample application zone 101 and either the conjugate zone 160 (FIGS. 6A and 6C) or the detection zone 105 (FIGS. 6B and 6D) of the test strip 100. In either case, the lysis zone 150 either overlaps the sample application zone 101 such that the lysis agent is pre-loaded in the sample application zone 101 (see FIGS. 6C and 6D) or the lysis zone 150 is located between the sample application zone 101 and the barrier in the blocking zone 170 such that the lysis agent is pre-loaded between the sample application zone 101 and the blocking zone 170 (see FIGS. 6A and 6B). Thus, lysis occurs before the sample reaches the blocking zone 170, and the barrier in the blocking zone 170 serves to slow or arrest those lysed materials effectively larger than the porosity of the barrier while permitting effectively smaller materials to pass more easily. Thus, the barrier provides a filtering effect and reduces interference with binding interactions in the conjugate 160 and detection zones 105. Selection of a specific barrier material depends on the analyte and the assay. Similar to FIGS. 5A through 5D, the detection zone 105 includes at least one test zone 102 and a control zone 104.

In another preferred embodiment, shown in FIGS. 7A through 7D, the sample is applied to the application zone 301 on a chromatography test strip 300. The sample passes a mucolytic zone 350, where one or more mucolytic agents have preferably been pre-loaded onto the test strip, and is eluted by the transport liquid. The mucolytic agent breaks down a mucosal sample in situ.

The chromatographic test strip contains a sample application zone 301, a mucolytic zone 350 containing a mucolytic agent, and a conjugate zone 360 containing at least one labeled binding partner that is eluted by and then able to migrate with a sample transport liquid (e.g. a buffer solution). The labeled binding partner is capable of specifically binding to an analyte of interest to form a conjugate which in turn is capable of specifically binding to another specific reagent or binding partner in the detection zone. Although not shown in these Figures, an absorbent pad, similar to the absorbent pad 1 shown in FIG. 1, as well as other known lateral flow assay components including, but not limited to, a waste zone, a carrier backing, a housing and an opening in the housing for result read out may optionally also be a component of the test strip 300 in this embodiment.

In a preferred embodiment, the mucolytic agent is localized in the mucolytic zone 350 between the sample application zone 301 and the conjugate zone 360. The mucolytic agent is preferably soluble or miscible in the sample transport liquid, and the mucolytic agent is solubilized and activated upon contact with the sample transport liquid. The sample transport liquid then contains both mucolytic agent in solution or suspension and sample components in suspension. Any mucolysis-susceptible components in a sample, then being exposed in suspension to the mucolytic agent, are broken down in situ. The running buffer then carries the analyte, including any mucolysis-freed components, to the detection zone 305.

Figure 7A:
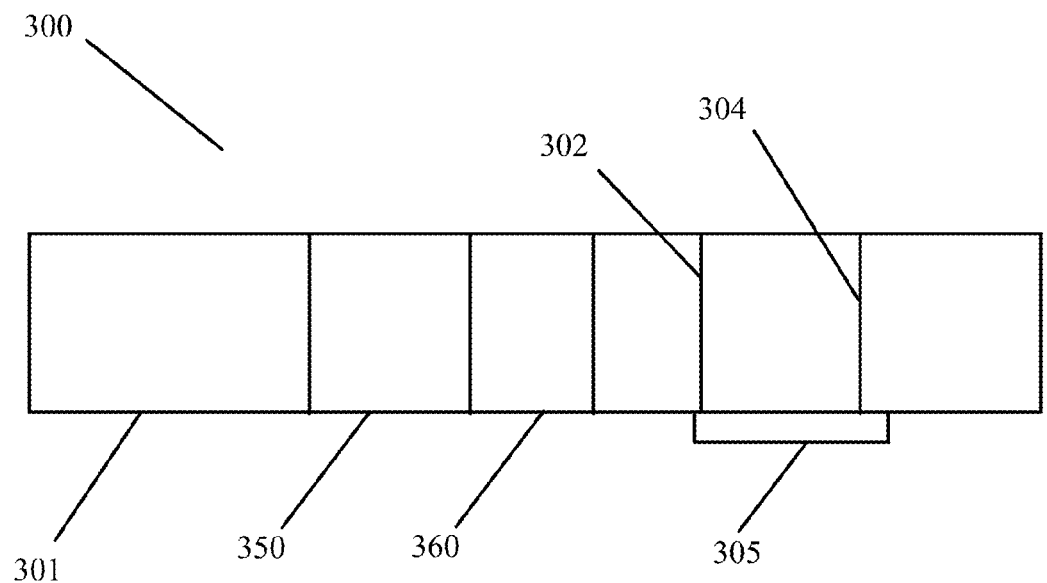
FIG. 7A shows a sample analysis device including a mucolysis zone located between a sample application zone and a conjugate zone in an embodiment of the present invention.
Figure 7B:
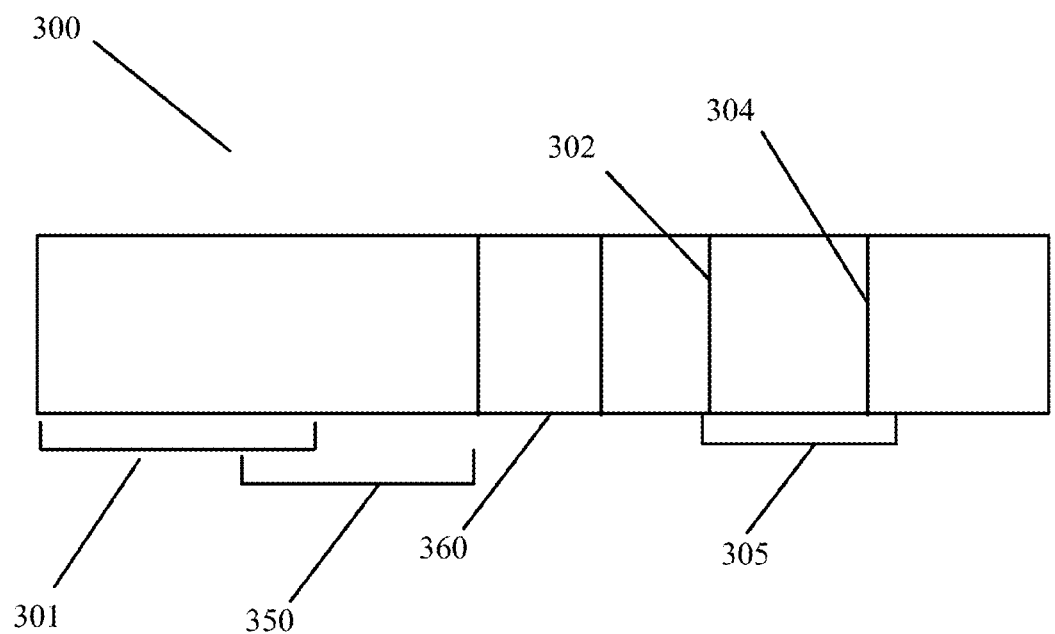
FIG. 7B shows a sample analysis device including a mucolysis zone overlapping a sample application zone in an embodiment of the present invention.
Figure 7C:
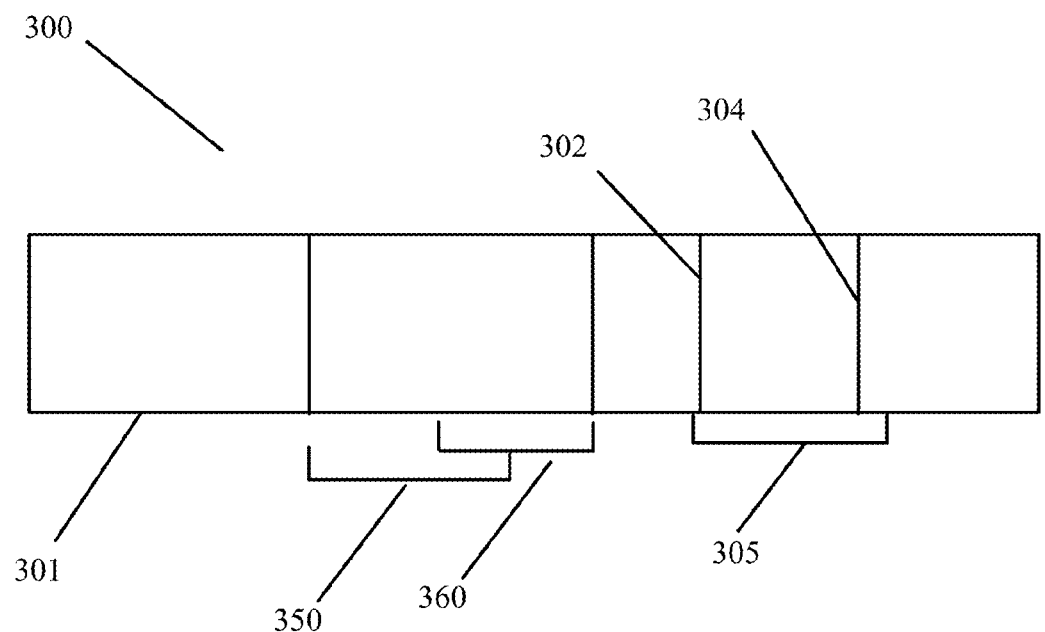
FIG. 7C shows a sample analysis device including a mucolysis zone overlapping a conjugate zone in an embodiment of the present invention.
Figure 7D:
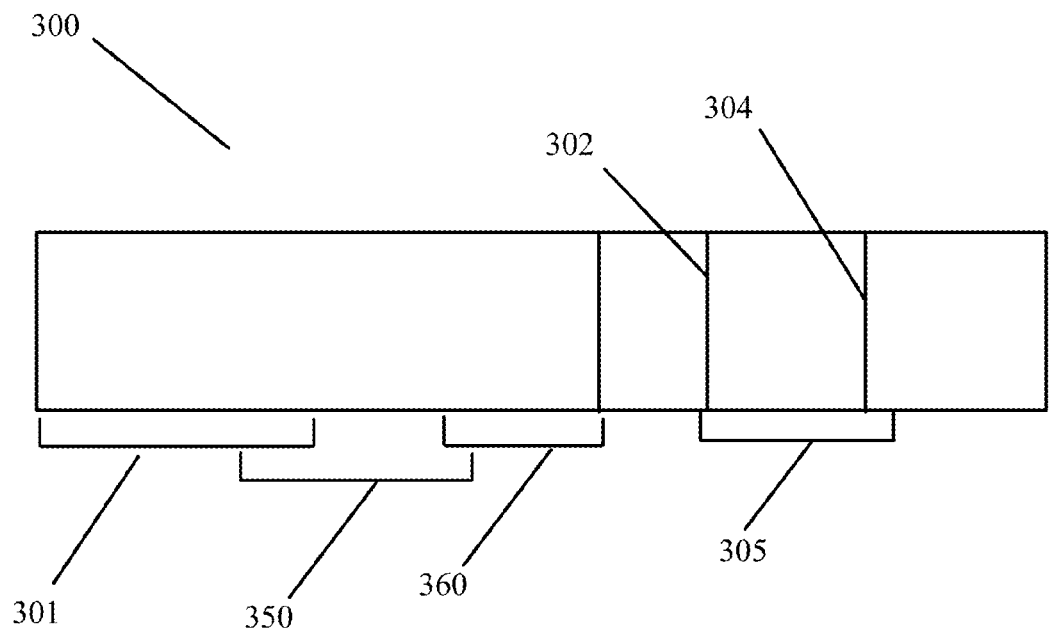
FIG. 7D shows a sample analysis device including a mucolysis zone overlapping a sample application zone and a conjugate zone in an embodiment of the present invention.
Figure 8A:
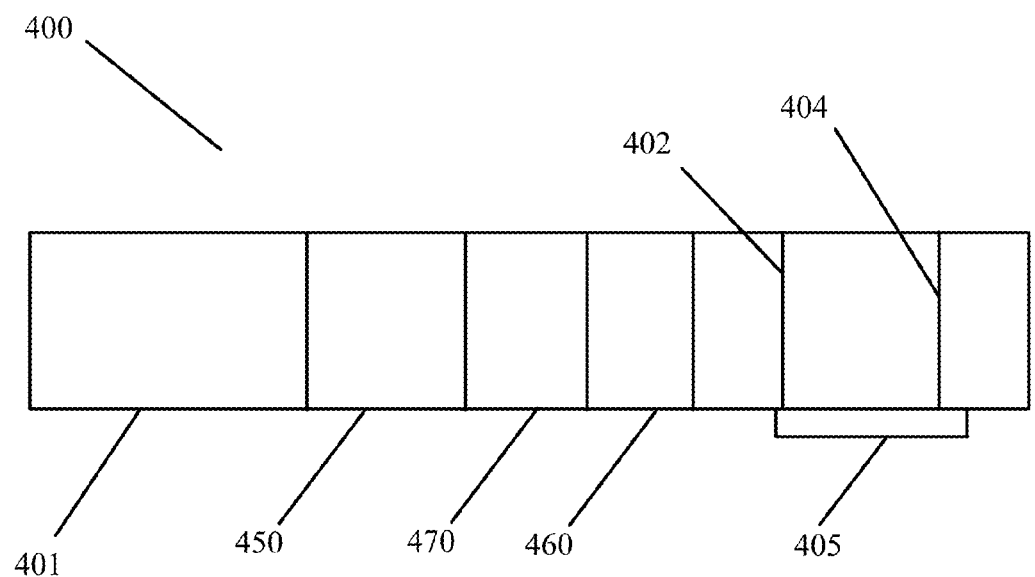
FIG. 8A shows a sample analysis device including a blocking zone located between a sample application zone and a conjugate zone in an embodiment of the present invention.
Figure 8B:
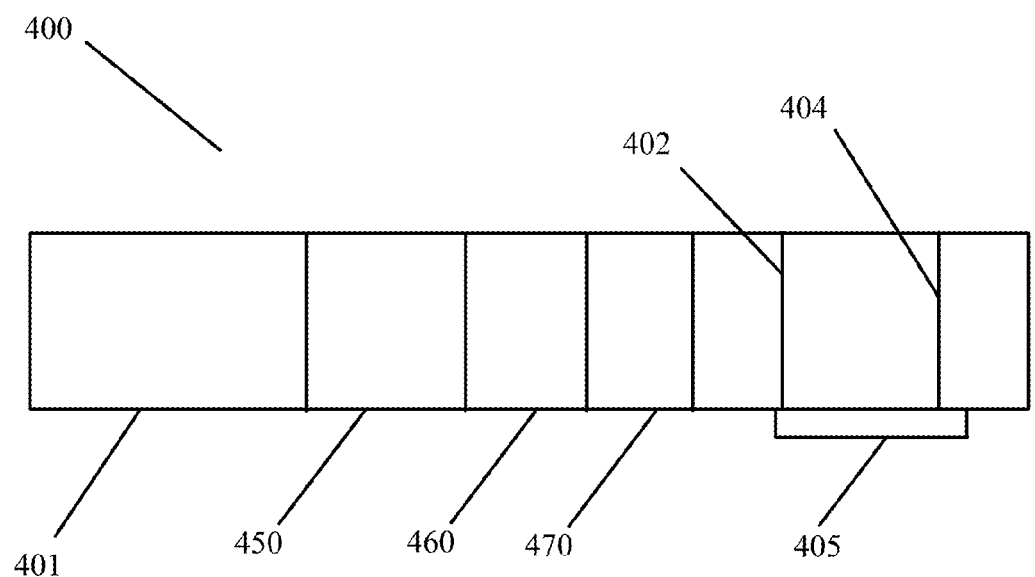
FIG. 8B shows a sample analysis device including a blocking zone located between a sample application zone and a detection zone in another embodiment of the present invention.
Figure 8C:
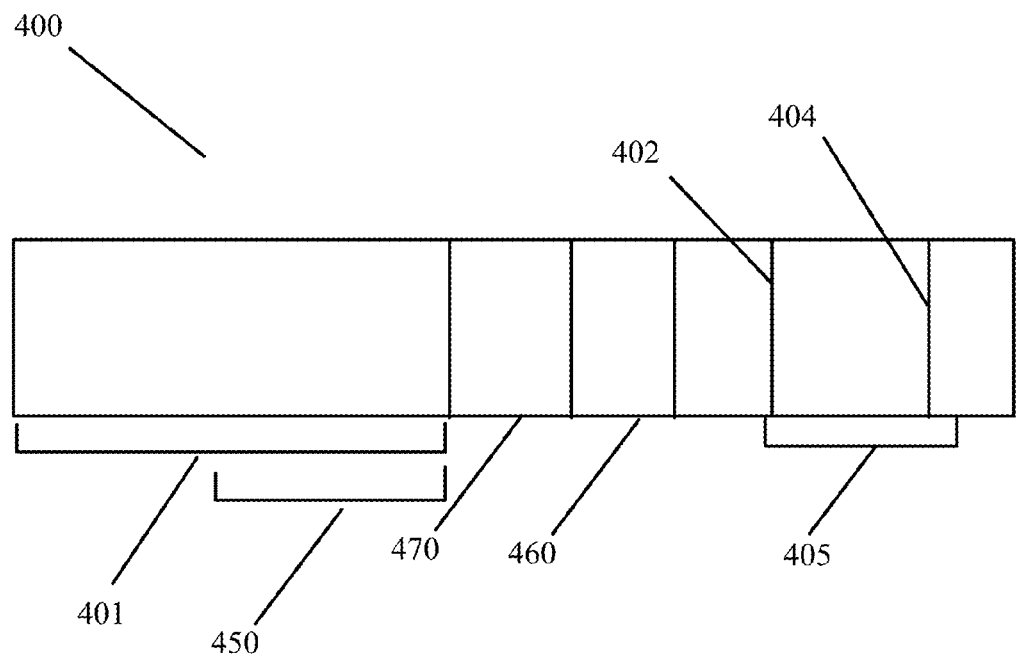
FIG. 8C shows a sample analysis device including a blocking zone located between a sample application zone and a conjugate zone in another embodiment of the present invention.
Figure 8D:
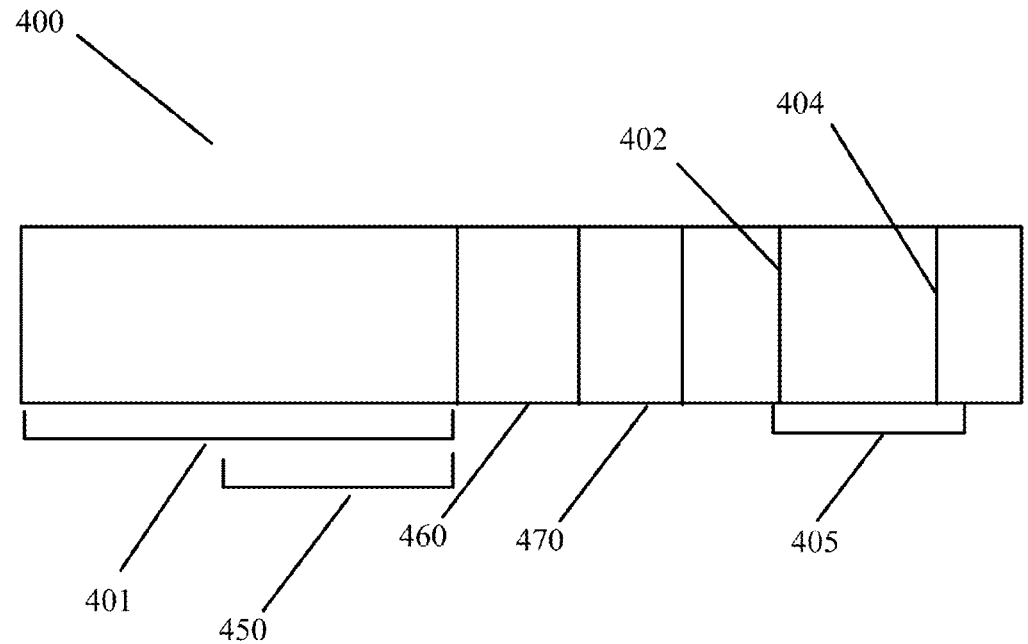
FIG. 8D shows a sample analysis device including a blocking zone located between a sample application zone and a detection zone in another embodiment of the present invention.

The mucolytic zone 350 is preferably located between the sample application zone 301 and the conjugate zone 360, as shown in FIG. 7A. In other embodiments, the mucolytic zone 350 overlaps the sample application zone 301, the conjugate zone 360 or both the sample application zone 301 and the conjugate zone 360 as shown in FIGS. 7B, 7C, and 7D, respectively. Note that the figures are schematic, and are not drawn to scale. The amount of overlap between the different zones (as shown in FIGS. 7B through 7D) may be highly variable.

The test strip 300 also includes a detection zone 305 containing a first section for detection of a first analyte, e.g. a test line 302, including an immobilized specific binding partner, complimentary to the conjugate formed in and arriving from the conjugate zone 360. Thus, at the test line 302, detection zone binding partners trap the labeled binding partners from the conjugate zone 360 along with their bound analytes. This localization of the analytes with their labeled binding partners gives rise to an indication at the test line 302. At the test line 302, the presence of an analyte is determined by qualitative and/or quantitative readout of the test line 302 indication resulting from the accumulation of labeled binding partners. Optionally, the detection zone 305 may contain further test lines to detect other analytes, as well as a control line/zone 304. The control line 304 indicates that the labeled specific binding partner traveled through the length of the assay, even though it may not have bound any analyte, thus confirming proper operation of the assay. As shown in FIGS. 7A through 7D, the control line 304 is preferably downstream of the test zone 302. However, in other embodiments, the control line 304 may be located upstream of the test zone 302.

In a preferred embodiment, the control line 304 includes an antibody or other recombinant protein which binds to a component of the elution medium or other composition being used in the test. In embodiments where nucleic acids are the targets, the control line 304 preferably includes a nucleic acid complementary to the labeled nucleic acid being used as a binding partner for the target nucleic acid.

Although only one test line is shown in the figures, multiple test lines are within the spirit of the invention. In some embodiments where there are multiple targets, the presence of each target preferably corresponds to a separate test line 302. In other embodiments where there are multiple targets, the presence of multiple targets may be indicated on the same test line such that the presence of more than one target has different characteristics than the presence of a single target. For example, the presence of multiple targets on the same test line may be visually indicated by a different color than the presence of each of the targets alone.

In other embodiments, it is possible to have one or more mucolytic agents in the running buffer itself. In these embodiments, there is no adverse effect on the conjugate zone which is downstream of where the buffer is added and the sample can either be upstream or downstream of the conjugate zone. A mucolytic agent in the running buffer can "target" the mucosal sample and break it up. In other embodiments, when the mucolytic agent is applied to the sample collection material 11 (see FIG. 3), then the conjugate zone may be upstream of the sample application zone.

In other embodiments, the sample collector, for example a swab member, can be treated with the mucolytic agent, as long as the agent is bio-compatible. For example, a swab member can be treated with NAC such that NAC is dried onto the swab before the sample is collected. Even if the NAC leaks into the body, for example into the eyes or other orifices, there is no harm because it is bio-compatible. Here, a sample with a mucous type membrane would be "clarified" as the mucous layer is broken down. This is particularly useful in samples used to test for sexually transmitted infections, for example, with organisms like *Chlamydia*. If NAC is used, there is no need to use one swab (or cotton ball) to "clean" the environment before the second swab collects the sample that will be tested for *Chlamydia*.

In another preferred embodiment, a barrier may be disposed in a "blocking zone" between the sample application zone and either the conjugate zone or the detection zone, preferably before the conjugate zone. In this case, the mucolytic agent is pre-loaded in the sample application zone or between the sample application zone and the barrier. Thus, mucolysis occurs before the sample reaches the barrier, and the barrier serves to slow or arrest any broken down materials effectively larger than the porosity of the barrier while permitting effectively smaller materials to pass more easily. Thus, the barrier provides a filtering effect and reduces interference with binding interactions in the conjugate and detection zones. Selection of a specific barrier material depends on the analyte and the assay.

A blocking zone barrier may be physical or biological. Examples of physical barriers include glass fiber matrices which inherently bind or trap erythrocytes and their cellular debris. Other physical matrices may be "sieve-type" matrices, as in a filtering system, where the small pore size blocks passage of cells but does allow passage of biomarkers.

In contrast, biological barriers are immobilized biological materials that specifically bind to ligands or receptors on a cell surface, preventing the cells from flowing further. Examples include antibodies, recombinant proteins, specific lectins, and receptors/ligands. Biological materials may also be combined into physical barriers such as glass fiber membranes.

FIGS. 8A through 8D show a barrier disposed in a "blocking zone" 470 between the sample application zone 401 and either the conjugate zone 460 (FIGS. 8A and 8C) or the detection zone 405 (FIGS. 8B and 8D) of the test strip 400. In either case, the mucolytic zone 450 either overlaps with the sample application zone 401 such that the mucolytic agent is pre-loaded in the sample application zone 401 (see FIGS. 8C and 8D) or the mucolytic zone 450 is located between the sample application zone 401 and the barrier in the blocking zone 470 such that the mucolytic agent is pre-loaded between the sample application zone 401 and the blocking zone 470 (see FIGS. 8A and 8B). Thus, mucolysis occurs before the sample reaches the blocking zone 470, and the barrier in the blocking zone 470 serves to slow or arrest those materials effectively larger than the porosity of the barrier while permitting effectively smaller materials to pass more easily. Thus, the barrier provides a filtering effect and reduces interference with binding interactions in the conjugate 460 and detection zones 405. Selection of a specific barrier material depends on the analyte and the assay. Similar to FIGS. 7A through 7D, the detection zone 405 includes at least one test zone 402 and a control zone 404.

The mucolytic agents may alternatively be upstream of the sample application zone (or overlapping the sample application zone on the upstream end of the strip), for example in the absorbent pad 1 shown in FIG. 1. In other embodiments, there may be multiple mucolytic agents and/or lysis agents in more than one location on the strip relative to the other components on the test strip, or in the running buffer.

In some preferred embodiments of the present invention, the lateral flow device of the present invention includes a sample-transporting liquid, which can be a buffer, a sample compressor, and a chromatography test strip containing one or several fleece materials or membranes with capillary properties through which sample flows. In a device and method of the invention, it is unnecessary to break down the cells in the sample prior to applying the sample to the test strip.

Figure 9:
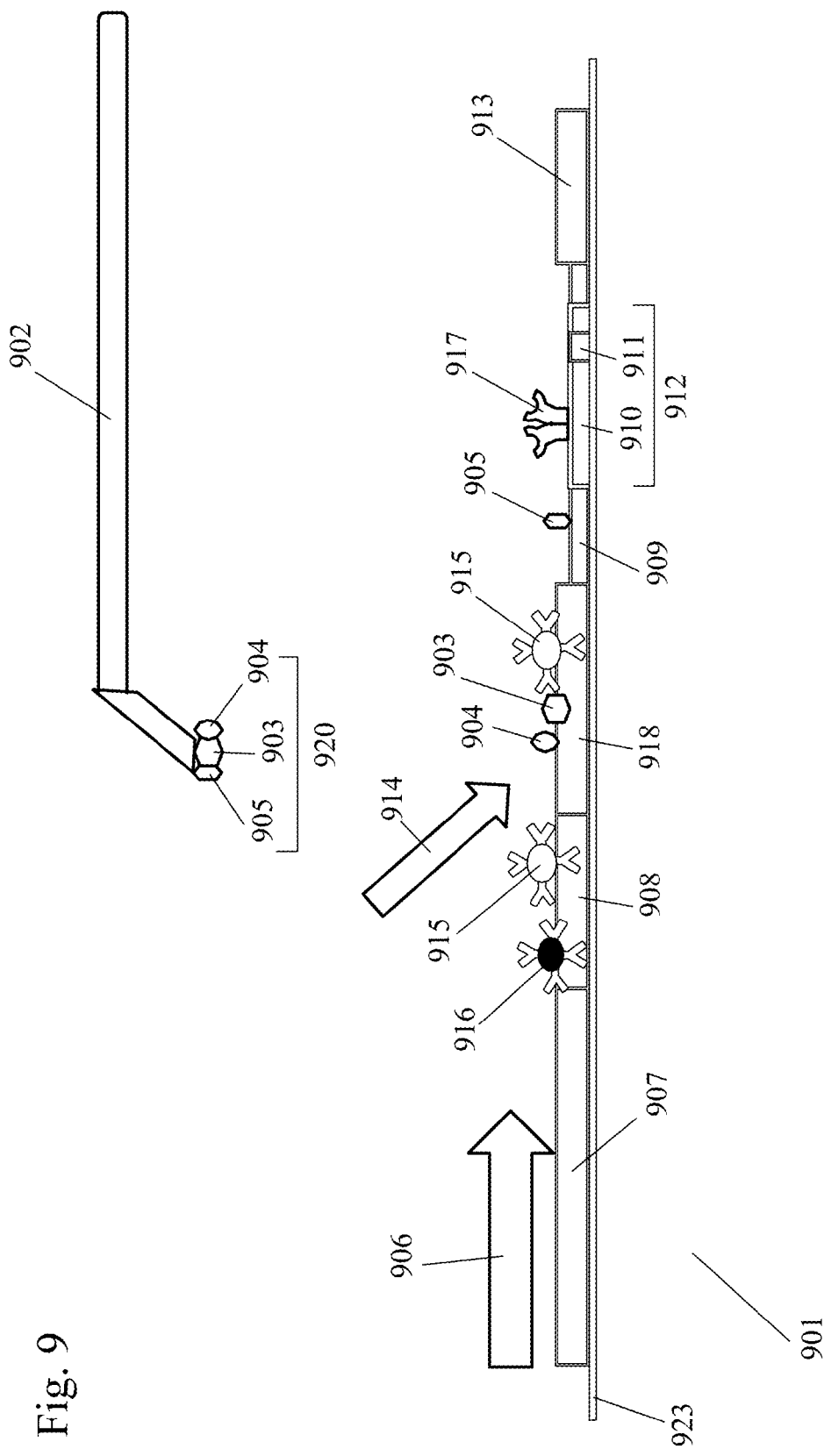
FIG. 9 shows a test strip and a sample collector in a lateral flow device.

FIG. 9 shows a sample analysis device (test strip) 901 and a sample collector 902. The sample collector 902 may be any type of sample collector 902 known in the art, for example the sample collector 902 could be a swab member. The sample 920 may include the analyte 903, as well as interfering particles 905 (which may include interfering proteins or interfering genes) and other interfering particles or cell debris 904. The sample analysis device 901 includes a conjugate zone 908 upstream of the sample application zone 918 in this figure. Although the conjugate zone 908 is shown upstream of the sample application zone 918 in this figure, the conjugate zone 908 may alternatively overlap the sample application zone 918 or be downstream of the sample application zone 918 within the spirit of the present invention. The sample application zone 918 is also a microfiltration zone, which preferably filters out cell debris and interfering particles 904 that are in the sample 920.

The conjugate zone 908 preferably includes both a mobile conjugate 915, which includes a portion that binds to the analyte 903 and a detectable label, and a control zone binding partner 916 with a detectable label, which may be, for example, a control zone antibody with a visual label. In some embodiments, the mobile conjugate is a test antibody conjugate with a visual label. The control zone binding partner 916 binds with an immobilized binding partner for it in the control zone 911 and indicates whether the test has run correctly. If the analyte 903 is present in the sample 920, the analyte binds to the conjugate 915, and the conjugate 915-analyte 903 complex travel to the test zone 910 in the detection zone 912. The analyte 903 then binds to an immobilized binding partner 917 for the analyte 903, to form the full "sandwich" in a sandwich-type assay.

The transfer of the sample from the sample collector 902 to the sample application zone 918 on the sample analysis device is preferably a direct transfer, i.e. the transfer takes place without pretreatment of the sample on the sample collector 902. In embodiments without pretreatment of the sample or the sample collector 902, pressure 914 is applied and microfiltration occurs in the region where the sample collector fleece directly contacts the fleece on the sample analysis device 901. The fibers of the fleece interlock to form a grating or physical interference. Thus, larger elements contained in the sample, for example cell debris and interfering particles 904 are held back and not eluted.

The sample application device 901 preferably also includes a blocking zone 909 that includes one or more capturing reagents. This blocking zone captures interfering proteins and/or genes 905 that may be in the sample 920. Capture of an interfering substance 904, 905 by one or more capturing reagents occurs when the capturing reagent interacts in some manner with the interfering substance to keep the interfering substance from interfering with the detection of the analyte. While a blocking zone 909 is shown in FIG. 9, the capturing reagents may be located in a capturing zone 909 made of materials that allow the capturing reagents to be mobile, in the elution medium, mixed and dried with the reagents, incorporated into the sample application zone, incorporated into the sample collector fleece material, and/or immobilized on an immobilizing material (for example, nitrocellulose) either as a line or a zone. Any of these or any combination of these may be used in the embodiments of the present invention, depending on the test and sample matrix.

The sample analysis device 901 also optionally includes an absorbent pad 907 upstream of the conjugate zone 908 and the sample application zone 918. Buffer is added and travels in the direction of the arrow 906 to elute the test components, including the sample 920, the conjugate 915, and the control zone binding partner 916, to the detection zone 912. The sample analysis device 901 also preferably includes a waste pad 913 at the downstream end of the device 901. The sample analysis device 901 may also optionally include a backing 923.

One or more lysis or mucolytic agents may be located (for example, dried on or otherwise included in the membranes making up these zones) in any of various locations on the test strip 901, including within the absorbent pad 907, the conjugate zone 908, the sample application zone 918 or the blocking zone 909, or overlapping any of the intersections between these areas on the strip. In other embodiments, the lysis or mucolytic agents may be on the sample collector 902 as long as the lysis or mucolytic agent being used is biocompatible. In yet another embodiment, one or more lysis or mucolytic agents may be placed where the sample application zone 918 meets the nitrocellulose membrane (use of a nitrocellulose membrane on the strip preferably begins in the blocking zone 909 in this figure; however, if there may alternatively be no blocking zone 909 on the strip). In preferred embodiments, the lysis or mucolytic agent overlaps or is upstream of the sample application zone 918. In still other embodiments, one or more lysis or mucolytic agent may be in the running buffer. If there are multiple lysis and/or mucolytic agents, they can be located in the same or different locations on the test strip or on the sample collector. A single lysis and/or mucolytic agent could be located in more than one location, if desired.

Figure 10A:
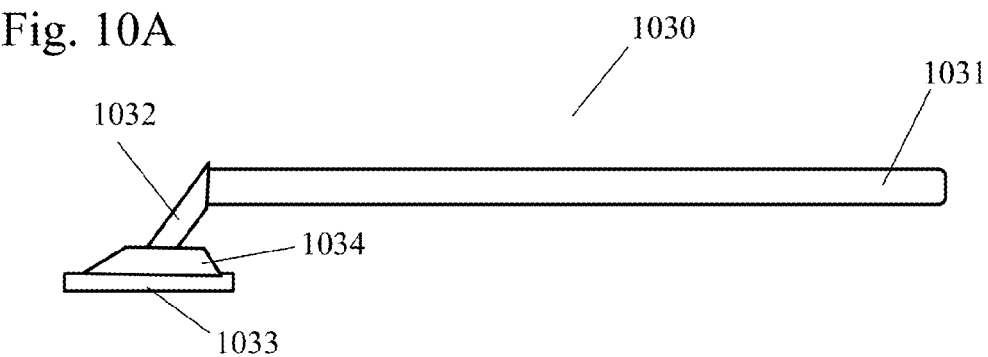
FIG. 10A shows a sample compressor in an embodiment of the present invention.
Figure 10B:
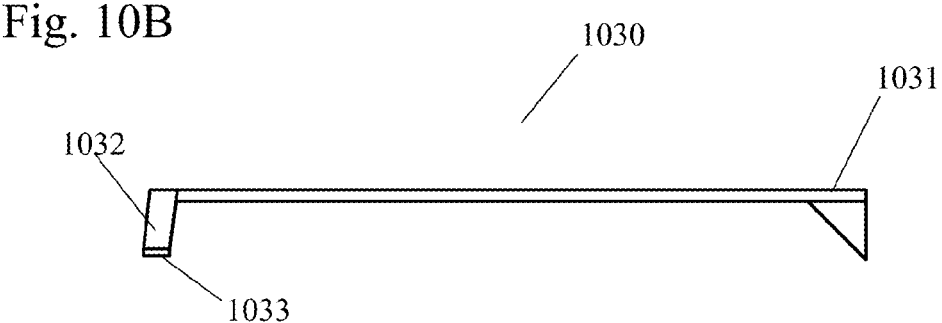
FIG. 10B shows another sample compressor in an embodiment of the present invention.

In some embodiments, the devices and methods of the present invention include a sample compressor 1030. Some schematic examples of sample compressors 1030 that could be used are shown in FIGS. 10A and 10B. The sample compressors 1030 preferably include a handle 1031, an extended portion 1032, and a pad portion 1033. In some designs, the sample compressor includes additional sections, such as a ledge portion 1034 that the pad portion 1033 is placed upon. While specific examples are shown in FIGS. 10A and 10B, any sample compressor 1030 that is able to exert pressure to transfer one or more components of the assay and the sample to the sample analysis device could be used in the embodiments of the present invention. In preferred embodiments, the conjugate 1036 (FIG. 11C) is pre-loaded and dried onto a pad 1033 that forms the conjugate zone. In some preferred embodiments, a labeled control 1061 (FIG. 11C) that is able to complex with a binding partner at the control zone is also pre-loaded and dried onto the pad 1033 of the sample compressor 1030. In other preferred embodiments, the second binding partner 1038 (FIG. 13C) for the analyte is located on the pad 1033. In some preferred embodiments, at least one lysis or mucolytic agent is pre-loaded and dried onto the pad 1033 that forms the conjugate zone. Any combination of the conjugate 1036, the second binding partner 1038, one or more lysis and/or mucolytic agents, or the control zone binding partner 1061 may be on the pad portion 1033 of the sample compressor 1030.

Figure 10C:
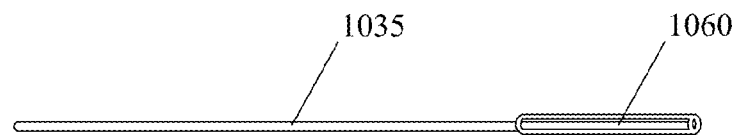
FIG. 10C shows a sample collector in an embodiment of the present invention.

FIG. 10C shows an example of a sample collector 1035. In this example, the sample collector 1035 is a swab member. The sample collector 1035 preferably includes a sample collection portion 1060, which is preferably made of fleece-type materials. In some embodiments, the sample collector 1035 is sterile. In some embodiments, one or more lysis or mucolytic agents that are biocompatible may be pre-loaded and dried onto the collection portion 1060 of the sample collector 1035. In one preferred embodiment, NAC is pre-loaded and dried onto the collector portion 1060 of the sample collector 1035.

Figure 11B:
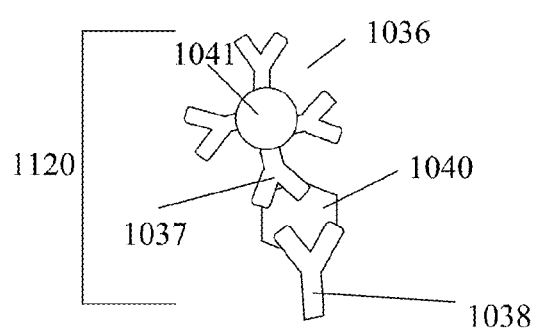
FIG. 11B shows a full sandwich including the analyte, the conjugate, and an immobilized binding partner in an embodiment of the present invention.

FIGS. 11A through 11C show one embodiment of a system with a sample compressor 1030, a sample collector 1035, and a sample analysis device (a test strip in the figure). The test strip preferably includes an absorbent pad 1042, a sample application zone 1044, a detection zone 1052, and an optional waste pad 1047. The test strip also preferably includes a carrier backing 1048. The detection zone 1052 preferably includes a test zone 1045, which includes an immobilized binding partner 1038 for the analyte 1040, as well as a control zone 1046. In this embodiment, the conjugate 1036 is on the sample compressor 1030. The first binding partner 1037, which is part of the conjugate 1036, from the sample compressor 1030 binds the analyte 1040 in the test sample to form a half sandwich, which is then transported to the second binding partner 1038 which is immobilized in a test zone 1045. The full sandwich 1120 that forms between the portion 1037 of the conjugate 1036 that binds to the analyte 1040, the analyte 1040, and the second binding partner 1038 is shown in FIG. 11B. In preferred embodiments, the pad 1033 on the sample compressor 1030 also includes a control zone binding partner 1061 with a detectable label. The control zone binding partner 1061 complexes with its binding partner in the control zone 1046. Including the control zone binding partner 1061 on the sample compressor 1030, instead of on the test strip or in the buffer as known in the prior art, permits the user to be sure that the components on the sample compressor 1030, which, in this embodiment include both the conjugate 1036 and the control zone binding partner 1061, have effectively transferred to the sample analysis device and thus ensures proper operation of the system.

In one example, both the first binding partner 1037 and the second binding partner 1038 are different antibodies to the analyte. The control zone binding partner 1061 is also preferably an antibody, and its binding partner at the control zone is an antigen (or vice versa). In other embodiments, specific binding partners may also be antigens capable of binding to antibodies against the analyte. Other types of binding partners are bioorganic macromolecules like aptamers or receptors, nanoparticles, or nucleic acids. The device shown in FIGS. 11A-11C of the present invention can be used for any binding assays, and can avoid the use of antibody/antigens or nucleic acids, for example, in ligand-receptor binding assays and enzyme-substrate binding assays.

In operation, the sample collector 1035 is placed such that the sample is directly above the sample application zone 1044. In some embodiments, placement of the sample collector 1035 above the sample application zone 1044 is not simultaneous with placement of the sample compressor 1030. In other words, in these embodiments, some of the sample is transferred to the sample application zone 1044 before the sample compressor 1030 is added to the vertical stack.

The sample compressor 1030 exerts pressure 1051 on the sample collector 1035, using pressure to transfer the sample, including the analyte 1040 (if present), and the conjugate 1036 onto the sample application zone 1044. If there is also a control zone binding partner 1061 on the sample compressor 1030, the control zone binding partner 1061 is also transferred. Note that the transfer is due to pressure, not due to flow or capillary action. Then, buffer 1043 is added to permit flow of the conjugate 1036-analyte 1040 complex (if present) to the detection zone 1052. An immobilized binding partner 1038 in the test zone 1045 then binds the analyte, forming the complete sandwich. Since the conjugate 1036 includes a label 1041, the complex that forms is detectable and indicates a positive result. Proper operation of the test also results in a detectable positive result in the control zone 1046 due to the interaction between the control zone binding partner 1061 and its immobilized partner in the control zone 1046.

One or more lysis or mucolytic agents may be located (for example, dried on or otherwise included in the membranes making up these zones) on the test strip in various locations including, in the absorbent pad 1042, in the sample application zone 1044, directly upstream of the detection zone 1052, in the detection zone itself, or within any of the intersections between these sections of the test strip. Alternatively, one or more lysis or mucolytic agents is pre-loaded and dried on the sample compressor 1030. One or more lysis or mucolytic agents may alternatively be located in the buffer. In other embodiments, the lysis or mucolytic agents may be on the sample collector as long as the lysis or mucolytic agent being used is biocompatible. In yet another embodiment, one or more lysis or mucolytic agents may be placed where the sample application zone 1044 meets the detection zone 1052 or where the sample application zone meets the nitrocellulose membrane. In preferred embodiments, the lysis or mucolytic agent overlaps or is upstream of the sample application zone 1044 or is located on the sample compressor 1030. If there are multiple lysis and/or mucolytic agents, they can be located in the same or different locations on the test strip, on the sample collector, or on the sample compressor. A single lysis and/or mucolytic agent could be located in more than one location, if desired.

In other embodiments, the conjugate zone contains both the binding partners for the analyte in the sample to form a "full sandwich". One of the binding partners preferably has a suitable marker such as biotin, avidin, lectin, a glycosyl moiety, a specific ligand, or a specific receptor. The other can be conjugated to the appropriate nanoparticles as mentioned below. The full sandwich is then captured at the test zone where the binding partner of the suitable marker, including, but not limited to, avidin for biotin, biotin for avidin, glycosyl moiety for lectin, lectin for the glycosyl moiety, a receptor for the ligand, or a ligand for the receptor, is immobilized.

FIG. 12A shows an example of a test strip in an embodiment of the present invention. The test strip preferably includes an absorbent pad 1042, a sample application zone 1044, a detection zone 1052, and an optional waste pad 1047. The test strip also preferably includes a carrier backing 1048. In this embodiment, the entire sandwich (first binding partner 1213-analyte-1040-second binding partner-1218) forms in the sample application zone 1044. The "full sandwich" 1214 is shown in FIG. 12B. The test zone 1045 in this embodiment includes an immobilized tag 1210 that binds to the tag 1219 of the second binding partner 1218. The immobilized tag 1210 does not bind directly to the analyte 1040; instead, it binds through an intermediary, the tag 1219 on the second binding partner 1218 for the analyte 1040.

In this embodiment, a first binding partner 1213, which is part of the labeled conjugate 1205, binds the analyte 1040 in the test sample to form half a sandwich. The second binding partner 1218 also includes a tag 1219. The second binding partner 1218 in this embodiment is preferably pre-loaded and dried on the sample application zone 1044 of the test strip, while the labeled conjugate 1205 is preferably pre-loaded and dried onto a labeled conjugate zone 1215 upstream of the sample application zone 1044. Alternatively, the second binding partner 1218 and/or the labeled conjugate zone 1215 may be located anywhere on the test strip upstream of the detection zone 1052 including, but not limited to, overlapping the sample application zone 1044, upstream of the sample application zone 1044, or between the sample application zone 1044 and the detection zone 1052. In one preferred embodiment, approximately 75-80% of the labeled 1209 conjugate 1205 is upstream of the sample application zone (with approximately 20-25% of the labeled conjugate 1205 overlapping the sample application zone 1044) and approximately 75-80% of the second binding partner 1218 is located downstream of the sample application zone 1044 (with approximately 20-25% of the second binding partner overlapping the sample application zone 44). Although not preferred, in other embodiments, either the labeled conjugate 1205, the second binding partner 1218, or both may be located in the buffer or pre-mixed with the sample before the sample is added to the test strip. In still other embodiments, any or all of the components overlap the detection zone 1052.

In some embodiments, both the first binding partner 1213 and the second binding partner 1218 are different antibodies to the analyte 1040. In other embodiments, specific binding partners may also be antigens capable of binding to antibodies against the analyte. Other types of binding partners are bioorganic macromolecules like aptamers or receptors, nanoparticles or nucleic acids. The device shown in FIG. 12A can be used for any binding assays, and can avoid the use of antibody/antigens or nucleic acids, for example, in ligand-receptor binding assays and enzyme substrate binding assays.

In one preferred embodiment, the second binding partner 1218 is tagged 1219 with biotin. In embodiments where the tag 1219 on the second binding partner 1218 is biotin, the immobilized tag 1210 in the detection zone 1052 is preferably avidin, neutravidin, or streptavidin. In other embodiments, the second binding partner 1218 is tagged 1219 with avidin, neutravidin, or streptavidin. In these embodiments, the immobilized tag 1210 in the detection zone 1052 is preferably biotin. Alternatively, the tag 1219 on the second binding partner 1218 may be a lectin and the immobilized tag 1210 may be a glycosyl moiety. For example, in some embodiments, the lectin is the Garden pea Lectin and the glycosyl moiety is an erythrocyte glycosyl unit. The tag on the second binding partner and the immobilized tag may be reversed within the spirit of the present invention. For example, the glycosyl moiety may be the tag on the second binding partner, with an immobilized lectin tag in the detection zone. In other embodiments, other receptors and ligands may be used for the tags.

In operation, a sample collector containing the sample is placed such that the sample is directly above the sample application zone 1044. In preferred embodiments, the sample has not been subject to pretreatment prior to application to the test strip. Instead, the sample is still in its native form.

The sample is transferred to the sample application zone 1044 of the test strip. A sandwich forms with the labeled conjugate 1205 as one piece of bread and the second binding partner 1218 as a second piece of bread, with the analyte 1040 in between them, when the three components come into contact with each other during flow 1043. The labeled conjugate 1205-analyte 1040 (if present)-second binding partner 1218 complex (a complete sandwich) flow to the detection zone 1052. An immobilized tag 1210 in the test zone 1045 then binds the tag 1219. Since the labeled conjugate 1205 includes a label 1209, the complex that forms is detectable and indicates a positive result. Proper operation of the test also results in a detectable positive result in the control zone 1046, preferably due to the interaction between a control line binding partner and its immobilized partner in the control zone 1046.

One or more lysis or mucolytic agents may be located (for example, dried on or otherwise included in the membranes making up these zones) in any of various locations on the test strip, including within the absorbent pad 1042, the labeled conjugate zone 1215, the sample application zone 1044, in the detection zone 1052, or overlapping any of the intersections between these areas on the strip. One or more lysis or mucolytic agents may alternatively be located in the buffer. In other embodiments, the lysis or mucolytic agents may be on the sample collector as long as the lysis or mucolytic agent being used is biocompatible. In yet another embodiment, one or more lysis or mucolytic agents may be placed where the sample application zone 1044 meets the detection zone 1052. In preferred embodiments, the lysis or mucolytic agent overlaps or is upstream of the sample application zone 1044. If there are multiple lysis and/or mucolytic agents, they can be located in the same or different locations on the test strip or on the sample collector. A single lysis and/or mucolytic agent could be located in more than one location, if desired.

In some preferred embodiments using tags, the detection zone includes an antibody against the tag. The antibody may be a monoclonal, polyclonal or single domain antibody. For example, when the tag is biotin, an anti-biotin antibody is immobilized in the test zone instead of avidin, neutravidin, or streptavidin.

Figure 13B:
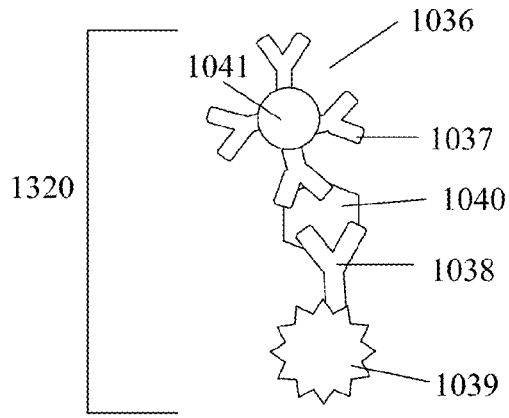
FIG. 13B shows a full sandwich including the analyte, the conjugate, and a tagged second binding partner in an embodiment of the present invention.

FIGS. 13A through 13C show an example of an embodiment of the system with a sample compressor 1030, a sample collector 1035, and a sample analysis device (a test strip in the figure). Similar to FIG. 11A-11C, the test strip preferably includes an absorbent pad 1042, a sample application zone 1044, a detection zone 1052, and an optional waste pad 1047. The test strip also preferably includes a carrier backing 1048. In this embodiment, the entire sandwich (first binding partner 1037-analyte-1040-second binding partner-1038) forms in the sample application zone 1044 (preferably before the addition of buffer). In some embodiments, placement of the sample collector 1035 above the sample application zone 1044 is not simultaneous with placement of the sample compressor 1030. In other words, in these embodiments, some of the sample is transferred to the sample application zone 1044 before the sample compressor 1030 is added to the vertical stack.

The test zone 1045 in this embodiment includes an immobilized tag 1050 that binds to the tag 1039 of the second binding partner 1038. In this embodiment, a first binding partner 1037, which is part of the conjugate 1036 and is preferably pre-loaded and dried on the pad 1033 of the sample compressor 1030, binds the analyte 1040 in the test sample to form a half sandwich. The second binding partner 1038 in this embodiment is also preferably pre-loaded and dried on the pad 1033 of the sample compressor. The second binding partner 1038 also includes a tag 1039.

The full sandwich 1320 that forms between the binding partner 1037 of the conjugate 1036, the analyte 1040, and the second binding partner 1038 in this embodiment (as well as the embodiments in FIGS. 14A-14B, 15A-15B, 16B, 16C, and 16D) is shown in FIG. 13B. In preferred embodiments, the pad 1033 on the sample compressor 1030 also includes a control zone binding partner 1061 (shown in FIG. 11C) with a detectable label. The control zone binding partner 1061 complexes with its binding partner in the control zone 1046. Including the control zone binding partner 1061 on the sample compressor 1030, instead of on the test strip or in the buffer as known in the prior art, permits the user to be sure that the components on the sample compressor 1030, which include both the conjugate 1036 and the control zone binding partner 1061, have effectively transferred to the sample analysis device and thus ensures proper operation of the system.

In one example, both the first binding partner 1037 and the second binding partner 1038 are different antibodies to the analyte. The control zone binding partner 1061 is also preferably an antibody, and its binding partner at the control zone is an antigen (or vice versa). In other embodiments, specific binding partners may also be antigens capable of binding to antibodies against the analyte. Other types of binding partners are bioorganic macromolecules like aptamers or receptors, nanoparticles, or nucleic acids. The device shown in FIGS. 13A-13C of the present invention can be used for any binding assays, and can avoid the use of antibody/antigens or nucleic acids, for example, in ligand-receptor binding assays and enzyme-substrate binding assays.

In one preferred embodiment, the second binding partner 1038 is tagged with biotin 1039. In embodiments where the tag 1039 on the second binding partner 1038 is biotin, the immobilized tag 1050 in the detection zone is preferably avidin, neutravidin, or streptavidin. In other embodiments, the second binding partner 1038 is tagged 1039 with avidin, neutravidin, or streptavidin. In these embodiments, the immobilized tag 1150 in the detection zone 1052 is preferably biotin. Alternatively, the tag 1039 on the second binding partner 1038 may be a lectin and the immobilized tag 1050 may be a glycosyl moiety. For example, in some embodiments, the lectin is the Garden pea Lectin and the glycosyl moiety is an erythrocyte glycosyl unit. The tag on the second binding partner and the immobilized tag may be reversed within the spirit of the present invention. For example, the glycosyl moiety may be the tag on the second binding partner, with an immobilized lectin tag in the detection zone. In other embodiments, other receptors and ligands may be used for the tags.

In operation, the sample collector 1035 is placed such that the sample is directly above the sample application zone 1044. The sample compressor 1030 exerts pressure 1051 on the sample collector 1035. The pressure transfers the sample (including the analyte 1040, if present), the conjugate 1036, and the tagged second binding partner 1038 onto the sample application zone 1044. If there is also a control zone binding partner 1061 on the sample compressor 1030, the control zone binding partner 1061 is also transferred. Note that the transfer is due to pressure, not due to flow or capillary action. Then, buffer 1043 is added to permit flow of the conjugate 1036-analyte 1040 (if present)-second binding partner 1038 complex (a complete sandwich) to the detection zone 1052. An immobilized tag 1050 in the test zone 1045 then binds the tag 1039. Since the conjugate 1036 includes a label 1041, the complex that forms is detectable and indicates a positive result. Proper operation of the test also results in a detectable positive result in the control zone 1046 due to the interaction between the control zone binding partner 1061 and its immobilized partner in the control zone 1046.

One or more lysis or mucolytic agents may be located (for example, dried on or otherwise included in the membranes making up these zones) on the test strip in various locations including, in the absorbent pad 1042, in the sample application zone 1044, directly upstream of the detection zone 1052, in the detection zone itself, or within any of the intersections between these sections of the test strip. Alternatively, one or more lysis or mucolytic agents is pre-loaded and dried on the sample compressor 1030. One or more lysis or mucolytic agents may alternatively be located in the buffer. In other embodiments, the lysis or mucolytic agents may be on the sample collector as long as the lysis or mucolytic agent being used is biocompatible. In yet another embodiment, one or more lysis or mucolytic agents may be placed where the sample application zone 1044 meets the detection zone 1052 or where the sample application zone meets the nitrocellulose membrane. In preferred embodiments, the lysis or mucolytic agent overlaps or is upstream of the sample application zone 1044 or is located on the sample compressor 1030. If there are multiple lysis and/or mucolytic agents, they can be located in the same or different locations on the test strip, on the sample collector, or on the sample compressor. A single lysis and/or mucolytic agent could be located in more than one location, if desired.

In another embodiment, the two binding partners for the analyte are located in such a way to achieve a "vertical sandwich" where the sample binds with the conjugate being compressed from the second plane and can bind simultaneously or concurrently with the other binding partner located on the strip in the plane of the strip. Thus a sandwiching of the analyte in the sample is achieved by binding to the partner from the conjugate delivered from above the plane of the strip and binding to the second binding partner located on the plane of the strip below the sample delivering material.

Figure 14A:
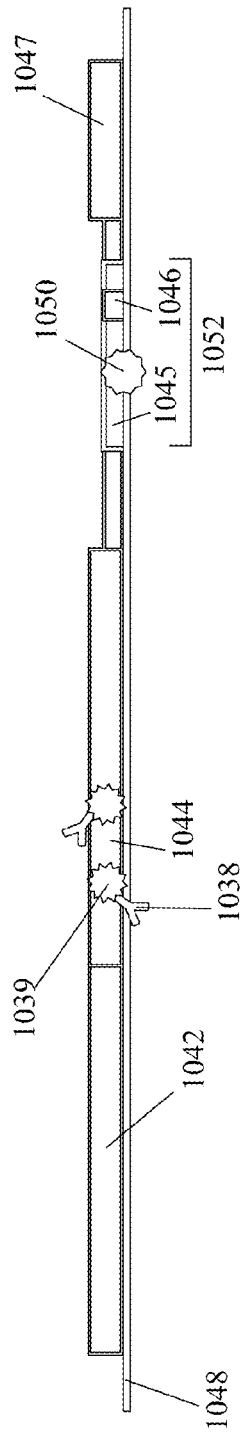
FIG. 14A shows yet another lateral flow test strip in an embodiment of the present invention.
Figure 14B:
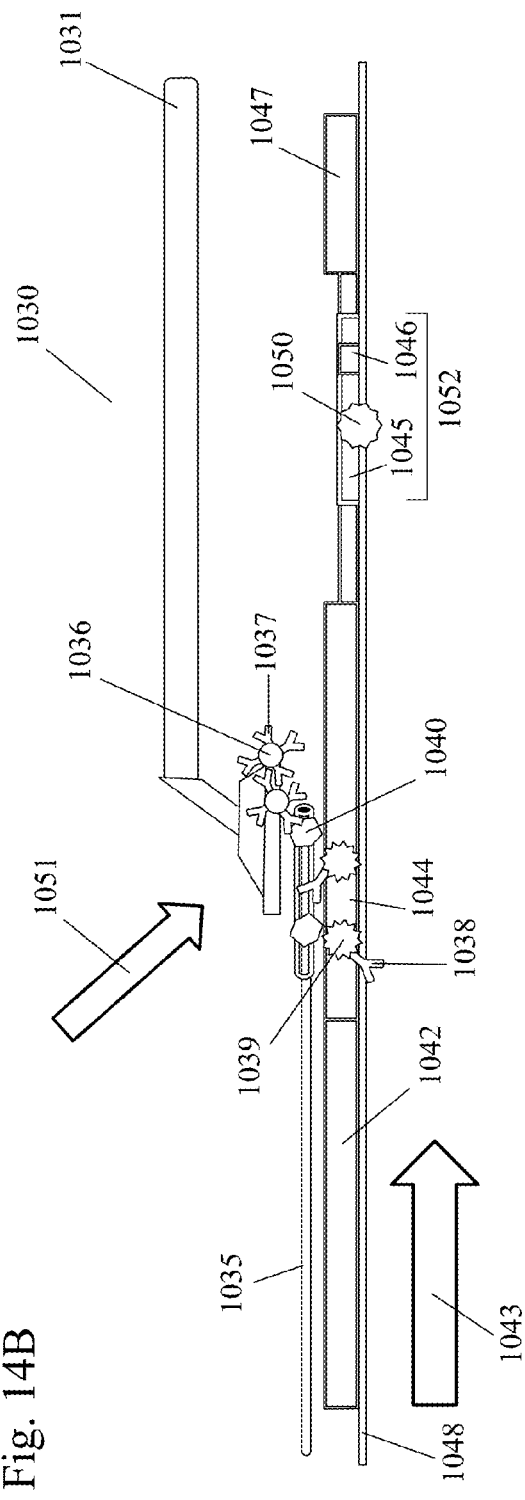
FIG. 14B shows a lateral flow device including the test strip of FIG. 14A, a sample collector, and a sample compressor in another embodiment of the present invention.

FIGS. 14A and 14B show another example of an embodiment of the system with a sample compressor 1030, a sample collector 1035, and a sample analysis device (a test strip in the figure). Similar to FIG. 11A-11C, the test strip preferably includes an absorbent pad 1042, a sample application zone 1044, a detection zone 1052, and an optional waste pad 1047. The test strip also preferably includes a carrier backing 1048. Similar to the embodiment shown in FIGS. 13A and 13C, in this embodiment, the entire sandwich (first binding partner 1037-analyte 1040-second binding partner 1038) forms in the sample application zone 1044. The test zone 1045 in this embodiment includes an immobilized tag 1050 that binds to the tag 1039 of the second binding partner 1038. In this embodiment, a first binding partner 1037, which is part of the conjugate 1036 and is preferably pre-loaded and dried on the pad 1033 of the sample compressor 1030, binds the analyte 1040 in the test sample to form a half sandwich. The second binding partner 1038 in this embodiment is preferably pre-loaded and dried on the sample application zone 1044 of the test strip. The second binding partner 1038 also includes a tag 1039. Alternatively, the second binding partner 1038 in this embodiment may be located anywhere on the test strip upstream of the detection zone including, but not limited to, overlapping the sample application zone, upstream of the sample application zone, and between the sample application zone and the detection zone.

In preferred embodiments, the pad 1033 on the sample compressor 1030 also includes a control zone binding partner 1061 (shown in FIG. 11C) with a detectable label. The control zone binding partner 1061 complexes with its binding partner in the control zone 1046. Including the control zone binding partner 1061 on the sample compressor 1030, instead of on the test strip or in the buffer as known in the prior art, permits the user to be sure that the components on the sample compressor 1030, which include both the conjugate 1036 and the control zone binding partner 1061, have effectively transferred to the sample analysis device and thus ensures proper operation of the system.

In one example, both the first binding partner 1037 and the second binding partner 1038 are different antibodies to the analyte. The control zone binding partner 1061 is also preferably an antibody, and its binding partner at the control zone is an antigen (or vice versa). In other embodiments, specific binding partners may also be antigens capable of binding to antibodies against the analyte. Other types of binding partners are bioorganic macromolecules like aptamers or receptors, nanoparticles, or nucleic acids. The device shown in FIGS. 14A-14B of the present invention can be used for any binding assays, and can avoid the use of antibody/antigens or nucleic acids, for example, in ligand-receptor binding assays and enzyme-substrate binding assays.

In one preferred embodiment, the second binding partner 1038 is tagged with biotin 1039. In embodiments where the tag 1039 on the second binding partner 1038 is biotin, the immobilized tag 1050 in the detection zone is preferably avidin, neutravidin, or streptavidin. In other embodiments, the second binding partner 1038 is tagged 1039 with avidin, neutravidin, or streptavidin. In these embodiments, the immobilized tag 1050 in the detection zone 1052 is preferably biotin. Alternatively, the tag 1039 on the second binding partner 1038 may be a lectin and the immobilized tag 1050 may be a glycosyl moiety. For example, in some embodiments, the lectin is the Garden pea Lectin and the glycosyl moiety is an erythrocyte glycosyl unit. The tag on the second binding partner and the immobilized tag may be reversed within the spirit of the present invention. For example, the glycosyl moiety may be the tag on the second binding partner, with an immobilized lectin tag in the detection zone. In other embodiments, other receptors and ligands may be used for the tags.

In operation, the sample collector 1035 is placed such that the sample is directly above the sample application zone 1044. The sample compressor 1030 exerts pressure 1051 on the sample collector 1035, using pressure to transfer the sample (including the analyte 1040, if present) and the conjugate 1036 onto the sample application zone 1044. A "vertical" sandwich forms with the conjugate 1036 as the top piece and the second binding partner 1038 as the bottom piece, with the analyte 1040 in between them. If there is also a control zone binding partner 1061 on the sample compressor 1030, the control zone binding partner 1061 is also transferred. Note that the transfer is due to pressure, not due to flow or capillary action. Then, buffer 1043 is added to permit flow of the conjugate 1036-analyte 1040 (if present)-second binding partner 1038 complex (a complete sandwich) to the detection zone 1052. An immobilized tag 1050 in the test zone 1045 then binds the tag 1039. Since the conjugate 1036 includes a label 1041, the complex that forms is detectable and indicates a positive result. Proper operation of the test also results in a detectable positive result in the control zone 1046 due to the interaction between the control zone binding partner 1061 and its immobilized partner in the control zone 1046.

One or more lysis or mucolytic agents may be located (for example, dried on or otherwise included in the membranes making up these zones) on the test strip in various locations including, in the absorbent pad 1042, in the sample application zone 1044, directly upstream of the detection zone 1052, in the detection zone itself, or within any of the intersections between these sections of the test strip. Alternatively, one or more lysis or mucolytic agents is pre-loaded and dried on the sample compressor 1030. One or more lysis or mucolytic agents may alternatively be located in the buffer. In other embodiments, the lysis or mucolytic agents may be on the sample collector as long as the lysis or mucolytic agent being used is biocompatible. In yet another embodiment, one or more lysis or mucolytic agents may be placed where the sample application zone 1044 meets the detection zone 1052 or where the sample application zone meets the nitrocellulose membrane. In preferred embodiments, the lysis or mucolytic agent overlaps or is upstream of the sample application zone 1044 or is located on the sample compressor 1030. If there are multiple lysis and/or mucolytic agents, they can be located in the same or different locations on the test strip, on the sample collector, or on the sample compressor. A single lysis and/or mucolytic agent could be located in more than one location, if desired.

FIGS. 15A and 15B show another embodiment of the present invention, where the sample compressor 1030 includes the second binding partner 1038 for the analyte 1040, coupled with a tag 1039, and the test strip includes the conjugate 1036, which includes both a first binding partner 1037 for the analyte 1040 and a detectable label 1041, and the immobilized tag 1050 that binds to the tag on the second binding partner in the test zone 1045. This embodiment operates similarly to the embodiment described with respect to FIGS. 14A and 14B, except that the "vertical" sandwich forms with the second binding partner 1038 as the top piece and the conjugate 1036 as the bottom piece, with the analyte 1040 in between them. Alternatively, the conjugate 1036 in this embodiment may be located anywhere on the test strip upstream of the detection zone including, but not limited to, overlapping the sample application zone, upstream of the sample application zone, or between the sample application zone and the detection zone.

One or more lysis or mucolytic agents may be located (for example, dried on or otherwise included in the membranes making up these zones) on the test strip in various locations including, in the absorbent pad 1042, in the sample application zone 1044, directly upstream of the detection zone 1052, in the detection zone itself, or within any of the intersections between these sections of the test strip. Alternatively, one or more lysis or mucolytic agents is pre-loaded and dried on the sample compressor 1030. One or more lysis or mucolytic agents may alternatively be located in the buffer. In other embodiments, the lysis or mucolytic agents may be on the sample collector as long as the lysis or mucolytic agent being used is biocompatible. In yet another embodiment, one or more lysis or mucolytic agents may be placed where the sample application zone 1044 meets the detection zone 1052 or where the sample application zone meets the nitrocellulose membrane. In preferred embodiments, the lysis or mucolytic agent overlaps or is upstream of the sample application zone 1044 or is located on the sample compressor 1030. If there are multiple lysis and/or mucolytic agents, they can be located in the same or different locations on the test strip, on the sample collector, or on the sample compressor. A single lysis and/or mucolytic agent could be located in more than one location, if desired.

FIGS. 16A through 16D are similar to FIGS. 11C, 13C, 14B, and 15B, respectively, except that the detection zone 1052 overlaps the sample application zone 1044 in these figures. The detection zone in these embodiments is preferably made of nitrocellulose. Although no lateral flow is strictly required to run the assay in these embodiments, at least a nominal amount of flow is preferred such that the sandwich is able to bind in the test zone and any unbound conjugate is washed out of the test zone. In one embodiment, instead of a running buffer being applied to an end of the test strip, a washing fluid may be applied directly to the test zone, either from above or from the side, for example using a water bottle. In one embodiment, the sample compressor and the sample collector are substantially transparent so that the test zone can be read without removal of the vertical stack from the test strip. Note that, while both the test zone 1045 and the control 1046 are shown within the sample application zone in these figures, in other embodiments the test zone 1045 could overlap the sample application zone 1044 while the control zone 1046 is downstream of the sample application zone 1044. If the control zone was laterally downstream from the sample application zone 1044, it would be necessary to add buffer to allow flow. In addition, it may be preferable to add a buffer, for example a buffer that includes silver, to enhance the signal from a positive result.

One or more lysis or mucolytic agents may be located (for example, dried on or otherwise included in the membranes making up these zones) on the test strip in various locations including, in the absorbent pad 1042, in the sample application zone 1044, overlapping or in the detection zone, or within any of the intersections between these sections of the test strip. Alternatively, one or more lysis or mucolytic agents is pre-loaded and dried on the sample compressor 1030. One or more lysis or mucolytic agents may alternatively be located in the buffer. In other embodiments, the lysis or mucolytic agents may be on the sample collector as long as the lysis or mucolytic agent being used is biocompatible. In yet another embodiment, one or more lysis or mucolytic agents may be placed where the sample application zone 1044 meets the detection zone 1052 or where the sample application zone meets the nitrocellulose membrane. In preferred embodiments, the lysis or mucolytic agent overlaps or is upstream of the sample application zone 1044 or is located on the sample compressor 1030. If there are multiple lysis and/or mucolytic agents, they can be located in the same or different locations on the test strip, on the sample collector, or on the sample compressor. A single lysis and/or mucolytic agent could be located in more than one location, if desired.

Figure 17A:
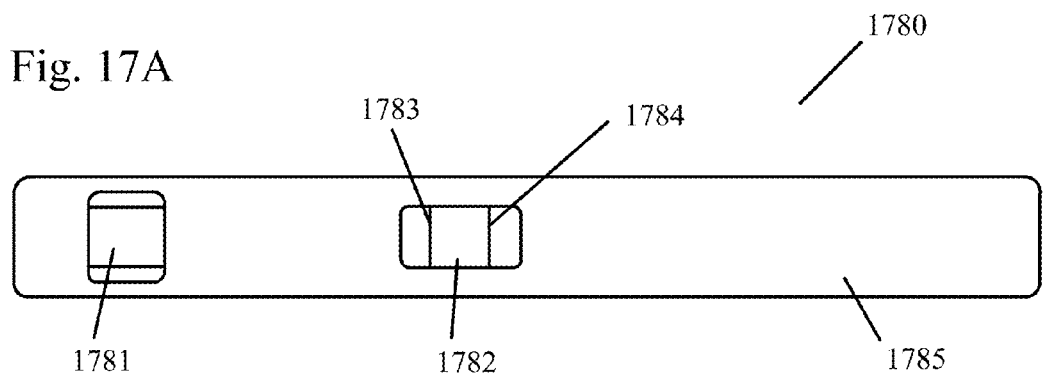
FIG. 17A shows a lateral flow device in an embodiment of the present invention.

A universal test strip 1780, as shown in FIG. 17A, may be used when the sample compressor 1030 includes both of the binding partners 1037, 1038 for the analyte 1040. The sample compressor 1030 and the sample collector 1035 would be transferred to the universal test strip 1780 at the sample window 1781. Since the elements specific to the analyte 1040 being tested are on the sample compressor 1030, the test zone 1783 in the viewing window 1782 of the universal test strip 1780 only needs to have a tag 1050 that complexes with the tag 1039 on the second binding partner 1038 for the analyte 1040. For example, when the second binding partner 1038 for the analyte 1040 is tagged 1039 with biotin, the test zone 1783 of the universal test strip 1780 would include avidin 1039, a binding partner for biotin. The universal test strip 1780 also preferably includes a control zone 1784 and a housing 1785. For the embodiments of FIGS. 16A through 16D, the test zone is located in the sample window 1781. In other embodiments, the suitable marker can be a nucleotide sequence that can hybridize with the suitable nucleic acid sequence immobilized at the test zone.

One or more lysis or mucolytic agents may be located (for example, dried on or otherwise included in the membranes making up these zones) anywhere on the universal test strip 1780 where it would come into contact with the sample and effectively break down the mucous membranes or otherwise lyse the sample. In one preferred embodiment with a universal test strip 1780, one or more lysis or mucolytic agents is pre-loaded and dried onto the pad of the sample compressor 1030. One or more lysis or mucolytic agents may alternatively be located in the buffer. In other embodiments, the lysis or mucolytic agents may be on the sample collector 1060 as long as the lysis or mucolytic agent being used is biocompatible. In preferred embodiments where the lysis or mucolytic agents are located on the universal test strip 1780, the lysis or mucolytic agent overlaps or is upstream of the location where the sample collector 1035 contacts the test strip 1780 (for example upstream of the sample window 1781). If there are multiple lysis and/or mucolytic agents, they can be located in the same or different locations on the test strip, on the sample collector, or on the sample compressor. A single lysis and/or mucolytic agent could be located in more than one location, if desired.

Although the sample compressor and the sample collector are shown as separate entities in FIGS. 9-17A, the pad 1033 of the sample compressor and the sample collector portion 1060 of the sample collector may be components of a single element within the spirit of the present invention. For example, the sample collector may be rotatably or flexibly or connected as part of a cartridge to the sample compressor, such that a sample can be collected from a patient with the sample collection portion without exposing the patient to the sample compressor pad and then the sample collection portion and sample compressor pad can be brought into contact for application to the sample application zone of the test strip by compression. The sample collector also may be rotatably or flexibly connected to the test cassette or may be inserted as a cartridge. In another embodiment, the sample may be forcibly injected directly onto the test strip prior to placing the compressor and/or conjugates into position. In yet another embodiment, the sample collector may contact the conjugates in an external cartridge that then snaps or inserts into a test cassette to bring the material in contact with the test strip.

Figure 17B:
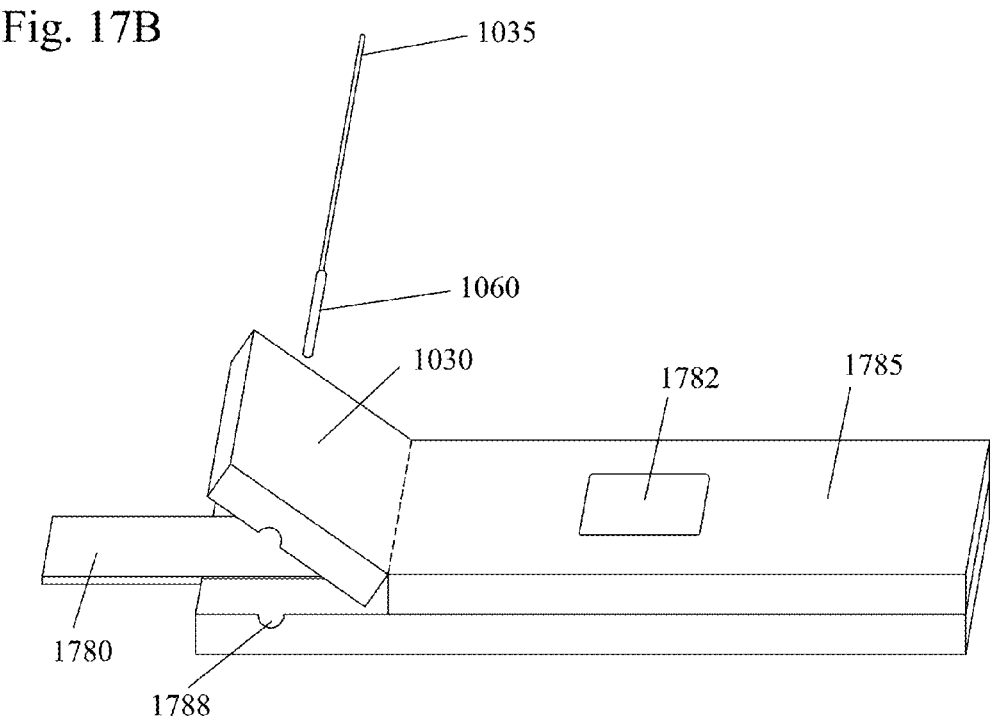
FIG. 17B shows another lateral flow device in an embodiment of the present invention.

In some embodiments, the sample compressor 1030 is rotatably connected to the housing 1785 as shown in FIG. 17B. While the hinge of the sample compressor 1030 is shown such that the sample compressor 1030 is rotated towards the downstream end of the strip when open, the housing could be designed such that the sample compressor 1030 is hinged to either side or in other directions within the spirit of the present invention. The sample collection portion 1060 of the sample collector 1035 is preferably inserted from the side such that it lines up with an insertion hole 1788 on the side of the housing 1785. However, the sample collector 1035 could be inserted in any direction depending upon the design of the housing. The sample compressor 1030 preferably includes a pad (not visible in FIG. 17B), with one or more assay components, located on the surface of the sample compressor facing the sample application zone of the test strip 1780. The sample compressor 1030 is then closed such that a compression pressure is applied to the vertical stack of the pad of the sample compressor, the sample collection portion, and the sample application zone to transfer the sample and the one or more assay components to the sample application zone of the test strip. While there is an absorbent pad sticking out of the housing at the far upstream end of the device in FIG. 17B, the length of the absorbent pad may vary. In fact, as long as buffer can be added at the upstream end (for example, through an application window in the housing), it is not necessary to have the absorbent pad extend significantly outside the housing. In this embodiment, there is no possibility of losing the sample compressor, and there is no need to align the sample compressor with the sample application zone when forming the vertical stack. One advantage of these embodiments is that they allow for a time lapse between sample application and the actual initiation of flow to the test zone. In other words, the sandwich can be pre-made, and the flow initiated much later.

Alternatively, the pad 1033 may be separate from the sample compressor within the spirit of the present invention. The pad may be on a binding partner applicator similar to the sample collector. In these embodiments, the binding partner applicator may be located between the sample collection portion and the sample application zone when the pressure is applied by the sample compressor to transfer the sample to the sample application zone.

Figure 18:
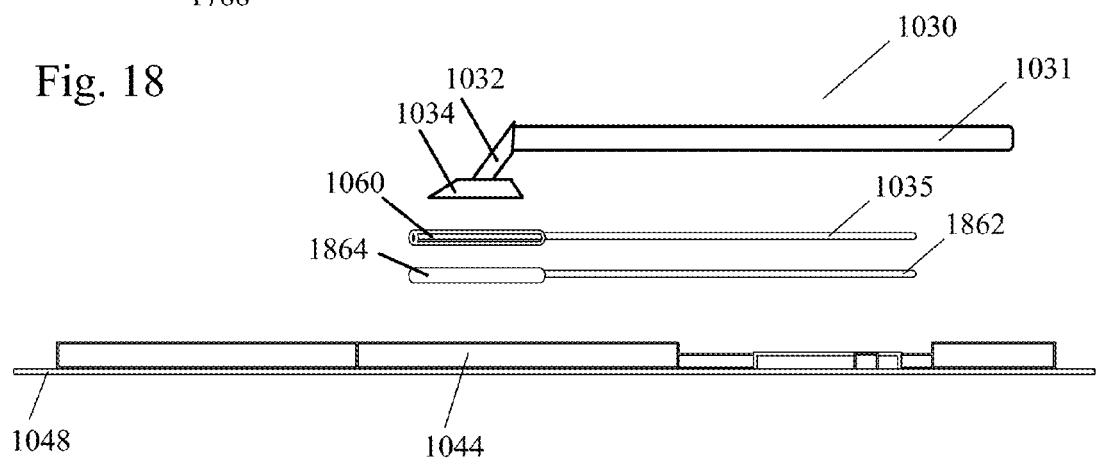
FIG. 18 shows a vertical stack in an embodiment of the present invention.

FIG. 18 shows a vertical stack including a sample compressor 1030, a sample collector 1035 with a sample collection portion 1060, a binding partner applicator 1862 with an applicator pad 1864, and a sample application zone 1044 of a test strip. While the binding partner applicator 1862 includes a handle in FIG. 18, the binding partner applicator 1862 could alternatively simply be a pad. The ledge portion 1034 of the sample compressor 1030 applies pressure to the sample collection portion 1060 loaded with a sample and the applicator pad 1864 loaded with at least one binding partner for an analyte to be tested for in the sample. The pressure preferably forces at least a portion of the sample from the sample collection portion 1060 to wet the applicator pad 1864, thereby mobilizing some of the binding partner such that at least some of the sample and some of the binding partner are transferred to the sample application zone 1044. In some embodiments, this transfer occurs without dilution. In embodiments with small sample volumes or viscous or solid samples, however, an additional liquid may be used to facilitate transfer of the sample and the binding partner to the test strip. In some embodiments, as shown in FIG. 18, the sample compressor has no pad, although a pad may be used to aid in transfer, such as by supplying additional liquid or buffer, within the spirit of the present invention. In some embodiments, as shown in FIG. 18, the sample collection portion 1060 is located between the sample compressor 1030 and the applicator pad 1864 in the vertical stack to aid in transfer of the binding partner to the test strip during compression. Alternatively, the applicator pad 1864 may be placed between the sample compressor 1030 and the sample collection portion 1060 within the spirit of the present invention. In embodiments where the full sandwich forms prior to reaching the test zone, two binding partner applicators (a separate applicator for each binding partner of the analyte) may be used, with the sample collection portion, the first applicator pad, and the second applicator pad being placed in any order on the vertical stack within the spirit of the present invention. Alternatively, a single binding partner applicator could include both of the binding partners for the analyte. In other embodiments, the sample, the first binding partner, and the second binding partner may be applied sequentially to the test strip in any order using the sample compressor within the spirit of the present invention.

In a method of applying a sample to a test strip of a lateral flow device, at least one external binding partner is first placed on the sample application zone of the test strip. The external binding partner may be located on an external pad. In embodiments where there are two analyte binding partners that bind the analyte prior to reaching the test zone, either one or both of the analyte binding partners may be added. A sample collector that includes the sample is placed in a vertical stack between the external binding partner and a sample compressor. The sample compressor applies pressure to the sample collector to transfer the external binding partner and at least a portion of the sample to the sample application zone. Alternatively, the external binding partner could be added and compressed by the sample compressor, then removed, before the sample collector is stacked above the sample application zone, where the sample is compressed onto the test strip. In another alternative embodiment, at least one external binding partner is placed in the vertical stack between the sample compressor and sample collector. Alternatively, the sample collector is added and compressed, then removed, and then the external binding partner is added and compressed onto the test strip. In other embodiments, the sample collector is in a vertical stack between a first external binding partner and a second external binding partner, and the sample compressor applies pressure to the vertical stack. In these embodiments, neither the strip nor the sample compressor has a specific analyte binding partner. The sample, the analyte binding partner, and the mobile control binding partner may also be applied to the sample application zone in multiple steps in any combination within the spirit of the present invention.

Alternatively, in a lateral flow device of the present invention, the sample compressor may be a universal sample compressor with no components specific to the analyte of interest. In one embodiment, the sample compressor contains no components of the assay. In embodiments with a control, the pad of the sample compressor contains only the mobile control zone binding partner. In these embodiments, one or more binding partner applicators include at least one binding partner for the analyte and become part of the vertical stack with the sample compressor and the sample collector when the sample is transferred to the sample application zone. The sample, the analyte binding partner, and the mobile control binding partner may also be applied to the sample application zone in multiple steps in any combination within the spirit of the present invention. In some embodiments, one or more lysis or mucolytic agents is also pre-loaded and dried onto the universal sample compressor.

In another embodiment of the present invention, the sample compressor 1030 also serves as the sample collector, and the pad 1033 of the sample compressor also serves as the sample collection portion. In this embodiment, the conjugate, the second binding partner, the control line binding partner, and/or any combination of the three, are preferably located on a back surface of the pad 1033, where the pad is attached to the sample compressor arm. In embodiments where sample collection needs to be performed sterilely, the sample compressor 1030 is then preferably sterilized by radiation prior to use as a sample collector. The sample is then collected using the front part of the pad so that the patient is not exposed to the conjugate or the second binding partner during sample acquisition. When the sample is applied to the sample application zone of the test strip, the pad is preferably compressed so that the sample mixes with the conjugate or the second binding partner and at least a portion of both is squeezed out onto the test strip. There may optionally be one or more lysis or mucolytic agents on the combination sample compressor/sample collector. If the lysis or mucolytic agent is biocompatible, the lysis or mucolytic agent can be located either on the front part or the back surface of the pad 1033. In other embodiments, the lysis or mucolytic agent is located on the back surface of the pad 1033.

The analytical tests discussed herein preferably permit a result while the patient is still being examined by the practitioner. The results of the tests are preferably determined within 20 minutes of transferring the sample to the device. In a preferred embodiment, the test result is obtained in 10 minutes or less after applying the sample to the device, and it is preferably read at approximately 10 minutes. In samples that are highly positive, a readout of the test zone (preferably a test line) is visible within approximately 1-5 minutes.

In some embodiments, the devices and methods of the present invention detect nucleic acids in a sample without the use of an amplification step for the target nucleic acid. In some embodiments, the detected nucleic acids are also quantified. The lateral flow detector may be used to detect a target nucleic acid sequence associated with any target virus, bacterium, fungus, or other pathogen, any genetic deficiency, or any other target nucleic acid in a sample. The target nucleic acid may be any nucleic acid including, but not limited to, DNA, an oligonucleotide, messenger RNA, or any other type of RNA. The assay is preferably run within a matter of minutes to a few hours after the sample is obtained, but the assay may be run at a later time such as at least 24 hours after obtaining the sample. The flow of the transport liquid in the detector may be gravity-dependent or as a result of capillary action or surface tension. The transport liquid may be applied by dipping the test strip in the transport liquid or the transport liquid may be contained in a test housing for the test strip.

A lateral flow nucleic acid detector in these embodiments may be uniplanar with a single sheet on a test strip for the detection zone. Alternatively, the detector may be multiplanar with multiple detection zones on multiple sheets in fluid communication for simultaneous assays for the same or different target nucleic acids from the same or different samples.

A sample for testing in these embodiments may be any sample expected to potentially include a target nucleic acid including, but not limited to, saliva, tears, cerebral spinal fluid, skin lesions, vaginal fluid, penile fluid, mucus, tissue, blood, urine, an environmental water sample, and a soil sample. In most cases, it is preferable to add a denaturant, lysis or mucolytic agent in situ to the sample in order to make the nucleic acids in the sample accessible to the first and second complexes. The denaturant, lysis or mucolytic agent is preferably pre-loaded onto a zone of the test strip or onto a sample compressor so that the sample may be applied directly to the test strip without a step of adding denaturant, lysis or mucolytic agent. The denaturant, lysis or mucolytic agent is pre-loaded onto the test strip or on the sample compressor in a location so that it frees the nucleic acids prior to the sample reaching the first complex on the test strip. The denaturant, lysis or mucolytic agent is preferably soluble or miscible in the transport liquid and located in the sample application zone or between the sample application zone and the zone where the first complex is pre-loaded.

In some embodiments, the sensitivity of visually read lateral flow assay tests is enhanced by adding a small quantity of fluorescing dye or fluorescing latex bead conjugates to the initial conjugate material. When the visible spectrum test line is visibly present, the test result is observed and recorded. However, in the case of weak positives that do not give rise to a distinct visual test line, a light of an appropriate spectrum, such as a UV spectrum, is cast on the test line to excite and fluoresce the fluorescing latex beads which are bound in the test line to enhance the visible color at the test line.

In some embodiments, the present invention provides a lateral flow assay that uses the lysis or mucolytic zone to help differentiate viral and bacterial infections. One situation where a lysis agent improves assay efficiency is in assaying for the presence of Human MxA, a 78 kDa protein which accumulates in the cytoplasm as a response to viral infection. The presence of this protein can help to distinguish between bacterial and viral infection in febrile children. In situ lysis using a combination of 1% to 6% weight/volume CHAPS and 0.5% to 2% weight/volume NP40 as the lysis agent improves detection of MxA in fresh or frozen whole blood.

A combined point of care diagnostic device tests markers for both viral and bacterial infection, and can effectively assist in the rapid differentiation of viral and bacterial infections, for example at the outpatient office or during an urgent care visit. This ability can dramatically reduce health care costs by limiting misdiagnosis and the subsequent overuse of antibiotics. Such a practice may limit antibiotic allergies, adverse events, and antibiotic resistance. The rapid result obtained from the test also permits a result while the patient is still being examined by the practitioner.

In one preferred embodiment, the marker for viral infection is MxA and the marker for bacterial infection is C-reactive protein (CRP). High MxA protein levels are strongly correlated with systemic viral infection and increased CRP is more associated with bacterial infections. The present invention includes a rapid infectious screening test for identifying MxA and CRP in samples. MxA is present in leukocytes (white blood cells). Therefore, the sample can be taken anywhere leukocytes are available, for example in a peripheral blood sample, nasopharyngeal aspirates, tears, spinal fluid, and middle ear aspirates.

In other embodiments, other markers for viral infection and/or bacterial infection may be used. For example, approximately 12% of host genes alter their expression after Lymphocytic Choriomeningitis Virus (LCMV) infection, and a subset of these genes can discriminate between virulent and nonvirulent LCMV infection. Major transcription changes have been given preliminary confirmation by quantitative PCR and protein studies and are potentially valuable candidates as biomarkers for arenavirus disease. Other markers for bacterial infection include, but are not limited to, procalcitonin, urinary trypsin inhibitor (uTi), lipopolysaccharide, IL-1, IL-6, IL-8, IL-10, ESR and an elevated WBC count (increased bands), Lactate, Troponin, vascular endothelial growth factor, platelet derived growth factor, cortisol, proadrenomedullin, macrophage migratory inhibitory marker, activated protein C, CD 4, 8, 13, 14, or 64, caspase, placenta derived growth factor, calcitonin gene-related peptide, high mobility group 1, copeptin, naturietic peptides, lipopolysaccharide binding protein, tumor necrosis factor alpha, circulating endothelial progenitor cells, complement 3a, and triggering receptor expressed on myeloid cells (trem-1).

In one embodiment, the infections being distinguished are respiratory infections. In other embodiments, other types of infections, which can be bacterial or viral, are differentiated using the system of the present invention. Some examples include, but are not limited to, encephalitis, meningitis, gastroenteritis, febrile respiratory illness (including bronchitis, pharyngitis, pneumonia), sinusitis, otitis media, urinary tract infections, and conjunctivitis.

The mucolytic agent may be in the running buffer that initiates the assay. In these embodiments, the mucolytic agent lyses the membranous material as it traverses through the strip.

In any of the embodiments described herein, the conjugate, for example gold or color dyed latex beads, the analyte binding partners, or the tags, can be treated with a mucolytic agent, for example NAC. Both mobile as well as immobile reagents or zones can be treated with mucolytic agents separately or in combination. These embodiments provide more opportunity for mucolysis.

The mucolytic agent may be localized in any position on the lateral flow test strip relative to the sample application zone, in the buffer, or on the sample collector or sample compressor device. In some embodiments, the mucolytic agent may be placed so that it is directly below the sample collector when the sample collector is applied to the lateral flow test strip. In some embodiments, the mucolytic agent may be localized at the end of the sample pad, or at the junction of the sample and/or conjugate pad and the detection zone membrane (such as a nitrocellulose membrane). The mucolytic agent may alternatively be deposited at the base of the detection zone membrane (such as a nitrocellulose membrane) where the sample and the conjugate complex can encounter it, resulting in further lysis of the sample in the complex. In embodiments with a sample compressor, the mucolytic agent may be located on the lateral flow test strip, the sample compressor, the sample collector, or in the buffer. The mucolytic agent in any of these embodiments could be added after the start of the assay.

In another embodiment, the sample collector collects the sample, and then is placed on the lateral flow test strip (or in the cassette in embodiments where a cassette is used). At that time, the mucolytic agent may be added to the sample collector and the strip. For example, one or two drops of the mucolytic agent may be added at this time. In embodiments with a sample compressor, this step occurs before the sample compressor compresses the sample collector. In one example where the target is MxA, this method would permit a blood sample to be lysed to release the leukocytic MxA. This method could be used in this example in any of the embodiments disclosed herein, with or without the use of a sample compressor.

In one preferred embodiment, the conjugate zone is upstream of the sample application zone and the sample being tested is blood. In this embodiment, the mucolytic agent could mucolyse the blood cells (e.g.—erythrocytes, leukocytes, platelets) and also make "holes" in the blood through which the microspheres of the conjugate can go through unhindered. Intact cells may hinder the movement of nanoparticles or microspheres of the conjugate going through a zone where they are located. When the mucolytic agent makes "holes" in those intact cells, the smaller nanoparticles can "go through" those holes.

EXAMPLE

One or more lysis agents are dried onto the sample application zone of a lateral flow strip. On a per strip basis, the lysis agent is made of approximately 2 microliters of 100 mM HEPES buffer (pH 8.0) containing 5% CHAP S and 2% NP-40 with 150 mM Sodium Chloride, 0.1% BSA, and 0.1% Sodium Azide (all percentages weight/volume). Up to 10 microliters of whole blood are then added to the sample application zone to be lysed in situ. MxA protein is released from inside white blood cells to react with an MxA monoclonal antibody on a visual tag (colloidal gold or visible latex beads). This complex traverses with a running buffer containing Triton X-100 and is captured by MxA monoclonal antibodies immobilized at the test line of the nitrocellulose membrane. This binding at the test line gives rise to a visible indication.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A lateral flow device for detecting an analyte in a sample comprising:
   a sample compressor comprising at least one mucolytic agent;
   a sample collector comprising a sample collection portion for collection of the sample;
   a test strip comprising a sample application zone and a test zone comprising an immobilized tag;
   a conjugate comprising a first binding partner for the analyte and a label; and
   a second binding partner for the analyte comprising a binding tag for binding to the immobilized tag of the test zone;
   wherein a component selected from the group consisting of the conjugate, the second binding partner and both the conjugate and the second binding partner is not located on the test strip prior to use of the lateral flow device; and
   wherein the sample compressor, the sample collector, and the test strip form a vertical stack to apply the sample to the test strip by compression;
   wherein the sample collector is located between the sample compressor and the test strip in the vertical stack.

2. A method of applying a sample to a test strip of a lateral flow device, the method comprising the steps of:
   a) placing a sample collector comprising a sample collection portion with the sample in a vertical stack between a sample compressor and a sample application zone of the test strip, wherein the sample compressor comprises at least one mucolytic agent; and
   b) applying a pressure to the sample collection portion using the sample compressor to transfer at least a portion of the sample to the sample application zone.

3. A lateral flow device for detecting an analyte in a sample comprising:
   a sample compressor;
   a sample collector comprising a sample collection portion for collection of the sample;
   a test strip comprising a sample application zone and a test zone comprising an immobilized tag;
   a conjugate comprising a first binding partner for the analyte and a label;
   a second binding partner for the analyte comprising a binding tag for binding to the immobilized tag of the test zone; and
   a mucolytic agent located in a location selected from the group consisting of: i) on the sample compressor; ii) on the sample collection portion of the sample collector and iii) on the test strip;
   wherein a component selected from the group consisting of the conjugate, the second binding partner and both the conjugate and the second binding partner is not located on the test strip prior to use of the lateral flow device; and
   wherein the sample compressor, the sample collector, and the component not on the test strip prior to use of the lateral flow device form a vertical stack to apply the sample to the test strip by compression.

4. The lateral flow device of claim 3, further comprising at least one lysis agent.

* * * * *